(12) United States Patent
Aben et al.

(10) Patent No.: US 9,138,506 B2
(45) Date of Patent: Sep. 22, 2015

(54) HPPE YARNS

(75) Inventors: Gerardus Aben, Montfort (NL); Edith Elisabeth Van Den Bosch, B-Riemst (BE); Claudia Maria Vaz, Maastricht (NL)

(73) Assignee: DSM IP ASSETS B.V., Heerlen (NL)

( * ) Notice: Subject to any disclaimer, the term of this patent is extended or adjusted under 35 U.S.C. 154(b) by 691 days.

(21) Appl. No.: 13/389,135

(22) PCT Filed: Aug. 5, 2010

(86) PCT No.: PCT/EP2010/061399
§ 371 (c)(1),
(2), (4) Date: Jul. 17, 2012

(87) PCT Pub. No.: WO2011/015620
PCT Pub. Date: Feb. 10, 2011

(65) Prior Publication Data
US 2012/0277772 A1    Nov. 1, 2012

(30) Foreign Application Priority Data

Aug. 6, 2009   (EP) .................................... 09167348
Nov. 13, 2009  (EP) .................................... 09175938

(51) Int. Cl.
*A61L 17/00*    (2006.01)
*A61L 17/14*    (2006.01)
(Continued)

(52) U.S. Cl.
CPC ............ *A61L 17/145* (2013.01); *A61L 17/005* (2013.01); *A61L 17/10* (2013.01); *C08L 23/06* (2013.01);
(Continued)

(58) Field of Classification Search
CPC ..... A61L 17/005; A61L 17/10; A61L 17/145; A61L 2300/404; A61L 2300/414; A61L 2300/606; A61L 2300/604; A61L 17/04; C08L 23/06

USPC .................. 606/228, 229, 230, 231, 232, 151
See application file for complete search history.

(56) References Cited

U.S. PATENT DOCUMENTS 4,712,553 A  * 12/1987  MacGregor ................... 606/231
6,403,666 B1    6/2002  Nakayama et al.
(Continued)

FOREIGN PATENT DOCUMENTS

| EP | 1 894 579 | 3/2008 |
| EP | 1 894 580 | 3/2008 |
| WO | WO 2007/092043 | 8/2007 |

OTHER PUBLICATIONS

Chinese Official Action dated May 14, 2014.
(Continued)

*Primary Examiner* — Katrina Stransky
(74) *Attorney, Agent, or Firm* — Nixon & Vanderhye P.C.

(57) ABSTRACT

The invention relates to a treated HPPE yarn characterized in that the treated HPPE yarn comprises: a porous polyolefin layer that adheres to a surface of a HPPE yarn and covers at least partly the surface of the HPPE yarn; a composition comprising an active agent and which composition is at least partially absorbed within the porous polyolefin layer. The invention further relates to an article comprising the treated HPPE yarn, a device comprising the treated HPPE yarn or the article. The invention also relates to a process for preparing the treated HPPE yarn or treated HPPE yarn structure or treated HPPE yarn configuration and use of the treated HPPE yarn or an article or a device comprising the treated HPPE yarn for automotive applications, marine applications, aerospace applications, medical applications, defense applications, sports/recreational applications, architectural applications, clothing applications, bottling applications, machinery applications.

20 Claims, 1 Drawing Sheet

(51) Int. Cl.
*C08L 23/06* (2006.01)
*A61L 17/10* (2006.01)

(52) U.S. Cl.
CPC ...... *A61L 2300/404* (2013.01); *A61L 2300/414* (2013.01); *A61L 2300/604* (2013.01); *A61L 2300/606* (2013.01); *D10B 2509/04* (2013.01)

(56) References Cited

U.S. PATENT DOCUMENTS

| | | | |
|---|---|---|---|
| 8,845,660 B2* | 9/2014 | Vaz et al. | 606/151 |
| 2003/0139775 A1 | 7/2003 | Grafton | |
| 2004/0167575 A1* | 8/2004 | Roby | 606/228 |
| 2005/0171604 A1 | 8/2005 | Michalow | |
| 2006/0083710 A1* | 4/2006 | Joerger et al. | 424/76.1 |
| 2006/0155329 A1 | 7/2006 | Grafton et al. | |
| 2007/0016251 A1 | 1/2007 | Roby | |
| 2007/0134305 A1 | 6/2007 | Zilberman | |
| 2007/0154707 A1* | 7/2007 | Simmelink et al. | 428/364 |
| 2008/0033485 A1* | 2/2008 | Roby | 606/230 |
| 2008/0051834 A1 | 2/2008 | Mazzocca et al. | |
| 2008/0058869 A1* | 3/2008 | Stopek et al. | 606/228 |
| 2008/0118734 A1 | 5/2008 | Goodwin et al. | |
| 2008/0287990 A1* | 11/2008 | Smit | 606/228 |
| 2009/0048628 A1 | 2/2009 | Marissen | |
| 2009/0299408 A1* | 12/2009 | Schuldt-Hempe et al. | 606/230 |
| 2009/0306709 A1* | 12/2009 | Snijder et al. | 606/228 |

OTHER PUBLICATIONS

International Search Report for PCT/EP2010/061399, mailed Oct. 25, 2010.
Written Opinion for PCT/EP2010/061399, mailed Oct. 25, 2010.
Notice of Reasons for Rejection, JP Application No. P2012-523335 (Dec. 2, 2014).

* cited by examiner

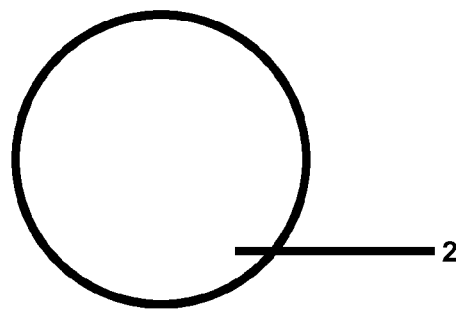
1a.
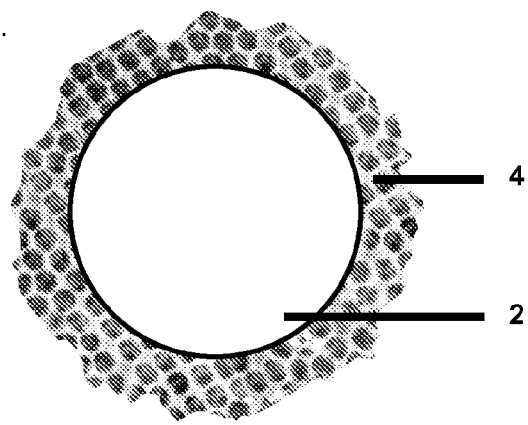
1b.
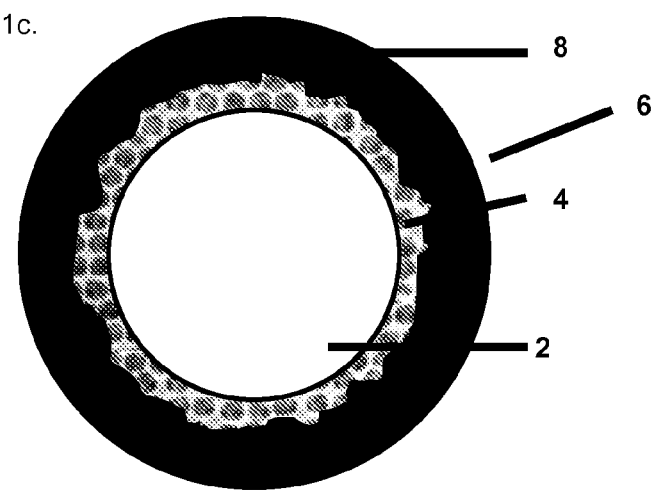
1c.

HPPE YARNS

This application is the U.S. national phase of International Application No. PCT/EP2010/061399 filed 5 Aug. 2010 which designated the U.S. and claims priority to EP Patent Application Nos. 09167348.3 filed 6 Aug. 2009 and 09175938.1 filed 13 Nov. 2009, the entire contents of each of which are hereby incorporated by reference.

The invention relates to a treated monofilament or multifilament yarn comprising a structural member of high performance polyethylene (HPPE), to a method for producing such yarn and to uses of this monofilament or multifilament yarn, in particular medical uses, such as use for non-absorbable surgical sutures.

A surgical suture is a stitch or series of stitches used by doctors or surgeons in order to hold tissue or bone(s) together by securing the edges of a surgical or traumatic wound. Over the years, surgical sutures have been made from a variety of materials, including flax, hair, cotton, silk, animal gut and synthetic materials like polyesters such as polyethylene terephthalate, segmented polyether-ester block copolymers, etc., polyamides and polyolefins, such as polyethylene or polypropylene. The surgical sutures made from synthetic materials can be used as either monofilament strands, i.e. monofilament surgical sutures, or as multifilament strands in a braided, twisted or other multifilament construction. Sutures can be divided into two broad categories, namely a) absorbable and b) non-absorbable, depending on the type of the material the surgical sutures are made from and the material's bio-absorptivity. By non-absorbable is meant that the suture is not dissolved, nor substantially degraded by the body's natural action after implantation. By absorbable is meant that the suture is dissolved or substantially degraded by the body's natural action after implantation. For example, surgical sutures made out of silk or polyethylene or polypropylene are non absorbable, whilst surgical sutures made from polyglactin or polylactic acid are absorbable surgical sutures. Non-absorbable surgical sutures are particularly suitable for load-bearing implants.

Surgical sutures intended to repair of body tissues are required to be non-toxic, capable of being readily sterilized, have good tensile strength (preferably as high as possible), be durable (have high fray resistance) and have acceptable knotting and knot characteristics. Nowadays, there is an additional need for surgical sutures and other surgical and/or medical articles or devices to present antimicrobial activity for extended time periods.

Surgical sutures coated with antimicrobial agents are commercially available for clinical use. At present polyglactin surgical sutures coated with antibiotics are sold under the tradename Coated VICRYL PLUS™ (polyglactin 910 braid) Suture (Ethicon, Somerville, N.J., U.S.A). The polymer used to make this surgical suture is poly(L-lactide-co-glycolide which is a copolymer consisting of 90% w/w glycolide and 10% w/w lactide. The VICRYL PLUS™ suture comprises 50% w/w polyglactin 730 which is a poly(L-lactide-co-glycolide a copolymer consisting of 35% w/w glycolide and 65% w/w lactide, 50% w/w calcium stearate (lubricant) and triclosan [chemical name: 5-chloro-2-(2,4-dichlorophenoxy) phenol] 150 µg/m suture, a well-known antibacterial drug used effectively in consumer products for more than 30 years. This suture creates an inhibitory zone around the suture in which bacteria are prevented from making colonies. The VICRYL PLUS™ suture is biocompatible and belongs to the category of absorbable sutures. It is used for general soft tissue approximation and/or ligation, except for ophthalmic, cardiovascular and neurological tissues. A disadvantage of this type of surgical sutures is that they cannot be used for bone repair due to their limited mechanical properties and in particular their tensile strength and E-modulus.

Monofilament or multifilament HPPE yarns, known in particular for their good mechanical properties such as high E-modulus and high tensile strength, are used in medical applications. Nevertheless, monofilament or multifilament HPPE yarns are not currently providing specific or additional protection against microorganisms. Sutures made from HPPE yarns can be very suitable not only for tissue repair applications but also for bone repair applications where the favorable mechanical properties of this type of yarns is beneficial since yarns with high tensile strength and resilience to friction and high mechanical stresses are required. Accordingly, there is the need to develop and use surgical sutures based on HPPE yarns that would present antimicrobial activity expressed over extended time period.

EP 1 293 218 A1 discloses an elongated non-absorbable suture strand for use as a surgical suture or ligament, which suture strand comprises a core of twisted strands of ultra-high molar mass polyethylene (UHMWPE) filaments, surrounded by a multifilament braided sheath also comprising UHMWPE filaments. The suture strand has excellent properties for its purpose, such as high tensile strength, flexibility and elasticity.

EP 1 743 659 A1 discloses monofilament surgical sutures made from a composition containing ultra high molecular weight polyethylene. Plasma etching of the ultra high molecular weight polyethylene is used as a treatment of the monofilament suture to provide a roughened surface which have varied morphologies that exhibit non-uniform pitting and porosity. These characteristics assist with the ability of the monofilament to hold a knot and assist with the adhesion of materials to the surfaces of the monofilaments. EP 1 743 659 A1 does not disclose compositions comprising antimicrobial agent or a fatty acid or a growth factor. In addition, EP 1 743 659 A1 is silent on the effect this treatment has on the mechanical properties of the treated monofilament in respect to the mechanical properties of the untreated one.

WO 02/076287 discloses fray resistant surgical sutures formed from one or more filaments, said surgical sutures are coated with oil, such as for example mineral or castor oil. The surgical sutures can be made from polyethylene. The surgical sutures may optionally contain other materials including colorants such as pigments or dyes, fillers or therapeutic agents, such as antibiotics, growth factors. Solution such as that described in WO 02/076287, although it can be applied for HPPE yarns, it offers limited—if any—mechanical stability of the coating that contains an oil and may contain materials including colorants such as pigments or dyes, fillers or therapeutic agents, such as antibiotics, growth factors. The limited—if any—mechanical stability of the coating of the WO 02/076287 is due to the limited adhesion of this coating onto a HPPE surface, a fact that derives from the well-known limited coatability of HPPE. Intrinsically untreated HPPE yarns present limited—if any—coatability. By limited coatability is meant that is difficult to cover partly or—most importantly—fully its surface with an organic coating composition applied by conventional application methods of untreated liquid coatings e.g. dipping, that has surface energy higher than that of polyethylene. It is known that the lower the surface energy of a surface the lower the wetting of its surface is, the more difficult it becomes to coat it. Therefore, the use of these particular and very tenacious yarns in applications where additional physical, chemical, biological and/or mechanical properties are required is restricted. So far, numerous attempts to directly adhere onto HPPE yarns organic coatings in order to impart to HPPE yarns additional physical, chemical, biological and/or mechanical properties, failed. The reason is that conventional coating approaches for the yarn, even if successful, lead to an undesired compromise of the favorable mechanical properties of the HPPE yarns such as the significant decrease of the high tensile strength of this type of yarns. Even when HPPE yarns were surface treated via conventional and well-known methods such as corona, UV-exposure in the presence or in the absence of a solvent, plasma etching, wet etching, etc, in order to increase at least the surface energy of the HPPE yarn, the thus treated HPPE yarns presented significantly inferior mechanical properties in comparison to the mechanical properties of untreated HPPE yarns.

US 20070134305 A1 discloses a composite structure composed of a fibril core and a polymeric coat encapsulating a bioactive agent while retaining the activity of the bioactive agent. The polymeric coat contains pores for entrapping the bioactive agent. The coats of US 20070134305 A1 are thick polymeric coatings having a thickness in the range from 10 μm (=10.000 nm) to about 2000 μm (=2.000.000 nm) and in certain cases can be even up to 1 cm (=10.000.000 nm). According to the US 20070134305 A1, the polymeric coating is formed via the application of a layer of an emulsion onto the surface of the fibril core. The application of the layer of the emulsion can be done via for example spraying, sputtering, brushing on the surface of the fibers or dipping the fibers in the emulsion. According to US 20070134305 A1 the mechanical properties of a coated fiber are inferior to the mechanical properties of an uncoated fiber.

As a consequence, the favorable array of mechanical properties of a HPPE yarn cannot be used to its full potential in applications where additional physical, chemical, biological and/or mechanical properties are to be combined with the favorable high E-modulus and high tensile strength of a HPPE yarn. So far, it is not possible to use monofilament or multifilament HPPE yarns in surgical sutures or in other type of medical article or medical device wherein the monofilament or multifilament HPPE yarns would present antimicrobial activity.

Another desirable property for a HPPE yarn would be the ability to offer controlled release of an active agent, such as for example an antimicrobial agent, to impart antimicrobial properties to a medical article or device which comprise HPPE yarn(s). The HPPE yarn or the article or the device then acts as a temporary reservoir for the agents, which are released after implantation of the article in a mammalian body. A frequent and commonly unaccepted problem occurs when trying to impart an additional property such as bioactivity to a material by modifying it, in that other desirable properties of the material, such as high tensile strength for instance, are compromised and at the same time the release of the bioactive substance is often insufficient.

There is a need in the industry for surgical sutures that would effectively utilize the high tensile strength of HPPE monofilament or filaments but at the same time would be able to offer controlled release of a bioactive agent such as for example an antimicrobial agent.

BRIEF DESCRIPTION OF THE DRAWINGS

The invention will be explained more fully below with reference to exemplary embodiments as well as the drawings, in which FIG. 1 shows in: 1a. a cross section of an HPPE yarn;

1b: a cross section of an HPPE and a porous polyolefin layer that adheres to the surface of the HPPE;

1c: a cross section of a treated HPPE yarn according to the present invention.

All the figures are highly schematic and not necessarily to scale, and they show only parts which are necessary in order to elucidate the invention, other parts being omitted or merely suggested.

DESCRIPTION OF THE DRAWINGS AND PREFERRED EMBODIMENTS

The object of the present invention is to address some or all of the problems or disadvantages identified herein. More particularly, It is the object of the present invention to provide a treated monofilament or multifilament HPPE yarn with improved properties. The improvement may for example be to provide a treated monofilament or multifilament HPPE yarn which will present at least comparable mechanical properties in respect to the mechanical properties of an untreated HPPE yarn and at the same time the treated HPPE yarn to deliver controlled release of an active agent such as for example a bioactive agent.

Therefore, broadly in accordance with the invention there is provided:

A treated HPPE yarn comprising:
   a porous polyolefin layer that adheres to a surface of a HPPE yarn and covers at least partly the surface of the HPPE yarn;
   a composition comprising an active agent and which composition is at least partially absorbed within the porous polyolefin layer.

The treated HPPE yarns of the present invention have comparable mechanical properties to those of untreated HPPE yarns and moreover present an enhanced adhesion and they are able to deliver active agents such as bioactive agents, thus presenting antimicrobial activity. In the context of the present invention the mechanical properties are understood to be elongation at break (%), E-modulus (GPa), and force-at-maximum break ($F_{max}$) (N).

The treated HPPE yarns of the present invention can also exhibit enhanced adhesion to organic coatings or inorganic coatings such as for example metal or metal oxide coatings, prolonged and controlled release of an active agent such as a bioactive agent for example an antimicrobial agent and/or a fungicide.

FIG. 1a shows in a schematic way a HPPE yarn, 2. As describe elsewhere, the HPPE yarn may be a monofilament or a multifilament construction and monofilament constructions encompass membranes, tapes and films. FIG. 1b shows a HPPE yarn, 2, and a porous polyolefin layer, 4, that adheres to the surface of a HPPE yarn, 2, and covers at least partly the surface of the HPPE yarn, 2. In FIG. 1c shows a treated HPPE yarn, 6, according to the invention. The treated yarn, 6, comprises the porous polyolefin layer, 4, that adheres to the surface of the HPPE yarn, 2, and covers at least partly the surface of the HPPE yarn, 2, and a composition, 8, comprising an active agent, which composition, 8, is at least partially absorbed or incorporated within the porous polyolefin layer, 4 to create a mechanical bond in addition to the chemical bond between the porous polyolefin layer, 4, and the composition, 8, comprising an active agent. For clarity, the physical dimensions of the objects presented in FIGS. 1a, 1b and 1c such as for example the relative layer thicknesses of the porous polyolefin layer and that of the composition are neither a true nor a proportional representation of the real physical dimensions of said objects. The physical dimensions of the objects presented in FIGS. 1a, 1b and 1c such as for example the layer thicknesses of the porous polyolefin layer and that of the composition, are explained in detail in the description of the present invention. Only the values and ranges of said physical dimensions, which are presented in the description of the present invention, are those which correspond to the true physical dimensions of the aforementioned elements.

According to the invention, the treated HPPE yarn is capable of sustained-, controlled- and time-release of an active agent. The release of an active agent may start upon implantation of for example the HPPE yarn, or at a particular time after implantation Preferably the delivery rate follows a bell-shaped curve over time, with an initially slow but exponentially increasing release rate rising to a maximal rate and wherein the rate then exponentially decreases over time, finally tailing off to zero. In the field of sustained-release of an active agent, it is generally considered desirable to avoid a large active agent release "burst" wherein the majority of the active agent is delivered in a short amount of time. This preferred release profile of an active agent is achieved by providing a treated HPPE yarn according to the invention.

The treated HPPE yarns of the present invention can also enhance the mechanical stability of the composition, thus contributing further to a better control over the release of the active agent.

The treated HPPE yarns of the present invention can also present some or all of the above mentioned properties without compromising the flexibility of a HPPE yarn.

By enhanced properties as used herein is meant that the relevant property of the treated HPPE yarn of the present invention is >+15% of the value of the known reference HPPE yarn described herein, more preferably >+17%, even more preferably >+20%, most preferably >+25%.

By comparable properties as used herein is meant that the value of the treated HPPE yarn of the present invention is within +/−15% of the value of the known reference HPPE yarn described herein, more preferably +/−12%, most preferably +/−10%.

The known reference HPPE yarn or yarn structure such as braids, for these comparisons is the commercially available HPPE yarn under the trade name Dyneema Purity® produced and marketed by DSM Dyneema B.V. or yarn structures such as braids made of this yarn.

The percentage differences for comparable and enhanced properties herein refer to fractional differences between the treated HPPE yarn of the invention and the known reference HPPE yarn where the property is measured in the same units in the same way (i.e. if the value to be compared is also measured as a percentage, it does not denote an absolute difference).

Unless the context clearly indicates otherwise, as used herein plural forms of the terms herein (for example metal, element, yarn, monofilament, multifilament, etc.) are to be construed as including the singular form and vice versa.

For all upper and lower boundaries of any parameters given herein, the boundary value is included in each range for each parameter. All combinations of minimum and maximum values of the parameters described herein may be used to define the parameter ranges for various embodiments and preferences of the invention.

In the context of the present invention the mechanical properties assessed were elongation at break (%), E-modulus (GPa), and force-at-maximum break ($F_{max}$) (N).

In the context of the present invention the terms "monofilament or multifilament HPPE yarns", "HPPE yarns" will be used interchangeably.

In the context of the present invention the terms "method" and "process" will be used interchangeably.

In the context of the present invention the terms "HPPE yarn" and "untreated HPPE yarn" will be used interchangeably.

In the context of the present invention, by "pre-treated HPPE yarn" is meant a HPPE yarn derived upon simultaneous plasma polymerisation and plasma etching, wherein a porous polyolefin layer adheres to the surface of the HPPE yarn and covers at least partly the surface of the HPPE yarn, but not having been treated with either the composition comprising the active agent, or with a lipid or with an alkyd or with a combination thereof.

In the context of the present invention, by "treated HPPE yarn" is meant a HPPE yarn, which HPPE yarn has been subjected to a physical and/or chemical process.

In the context of the present invention, by "treated HPPE yarn structure" is meant a HPPE yarn structure encompassing structures derived upon structuring treated HPPE yarns or structures derived upon structuring HPPE yarns which latter structures were subjected to a physical and/or chemical process.

In the context of the present invention, by "treated HPPE yarn configuration" is meant a HPPE yarn configuration encompassing configurations derived upon configuring treated HPPE yarns or configurations derived upon configuring HPPE yarns which latter configurations were subjected to a physical and/or chemical process.

In the context of the present invention the terms "filament" or "yarn", will be used interchangeably.

By layer is meant a thickness of some substance, such as a stratum or a coating on a surface.

By porous layer is meant a layer which is at least permeable to gases. Porosity is the measure of how porous a material is and it is a measure of the void spaces in a material. Porosity is a fraction of the volume of voids over the total volume, between 0-1, or as a percentage between 0-100%.

By polyolefin layer is meant a layer which comprises a polyolefin (an equivalent term is polyalkene; this is a more modern term, although polyolefin is still used in the petrochemical industry), which is a polymer produced from a simple olefin (also called an alkene with the general formula $C_nH_{2n}$) as a monomer or a mixture of alkenes. According to the present invention the backbone of a polyolefin comprises carbon and hydrogen atoms and said polyolefin can be functionalized with functional groups, for example amino and/or hydroxyl and/or carboxyl groups. According to the present invention the backbone of a polyolefin substantially consists of carbon and hydrogen atoms and it can be functionalized with functional groups, for example amino and/or hydroxyl and/or carboxyl groups. For example, polyethylene is the polyolefin produced by polymerizing the alkene, ethylene. Polypropylene is another common polyolefin which is made from the olefin propylene. Preferably the alkene monomer used is ethylene. Exemplary alkene monomers include but are not limited to ethylene, propylene, etc. The functionalization of a polyolefin can be achieved when for example the plasma polymerization of an olefin or a mixture of olefins is combined with plasma etching wherein the gas used in the plasma etching is selected from the group consisting of carbon dioxide ($CO_2$) and ammonia ($NH_3$) (see Examples 3-12). M. M. Hossain et al. (Plasma Process. Polym. 2007, 4, 471-481, incorporated herein by reference) describe a technique based on simultaneous plasma polymerization and plasma etching for producing and depositing such porous layer on polyester textiles.

The porous polyolefin layer adheres to the surface of a HPPE yarn. By this is meant the ability of the porous polyolefin layer to establish firm contact with the surface of the HPPE yarn without skidding or slipping. In the context of the present invention and in a broader sense, by adhesion is meant the ability of a substance or a material to establish firm contact with a surface on which the substance or the material is in contact.

By composition is meant the combining of distinct chemical substances to form a whole. It will be understood that the total sum of any quantities expressed herein as percentages cannot (allowing for rounding errors) exceed 100%. For example the sum of all distinct chemical substances of which the composition of the invention (or part(s) thereof) comprises may, when expressed as a weight (or other) percentage of the composition (or the same part(s) thereof), total 100% allowing for rounding errors. However where a list of components is non exhaustive the sum of the percentage for each of such distinct chemical substances may be less than 100% to allow a certain percentage for additional amount(s) of any additional distinct chemical substances that may not be explicitly described herein. In the context of the present invention the composition should comprise an active agent and may preferably comprise a lipid or an alkyd or an oxidizing alkyd, as these as described herein, or mixtures thereof.

By active agent is meant a compound which produces an intended action or effect.

For the purposes of the present invention, a yarn is herein understood to mean a product or an article the length dimension of which is much greater than its transverse diameter that can be used as an end-product or for making various other articles or devices thereof. Therefore a yarn herein includes both a yarn made of a plurality of monofilaments and a yarn made of a single monofilament.

A monofilament is herein understood to mean a filament obtainable from a single spin hole. It is noted that a monofilament herein includes a fused multifilament yarn having some monofilament characteristics, such as the one described in EP 0 740 002 A1, incorporated herein by reference. For the purposes of the present invention, a monofilament is an elongated body the length dimension of which is much greater than its transverse diameter.

In a special embodiment, the monofilaments preferably have a substantially circular or elliptical cross-section. In comparison to the yarn which is a monofilament, a multifilament yarn is herein understood as an elongated body comprising a plurality of individual monofilaments which are arranged to make up a single yarn. Multifilaments also encompass an array of monofilaments or multifilaments such as a unidirectional (UD) monolayers. Unidirectional monolayers are produced by positioning a plurality of HPPE yarns in parallel arrangement on a suitable surface and embedding the fibres in a suitable matrix material. The thus prepared network consists of a plurality of yarns unidirectionally aligned in parallel to one another along a common yarn direction.

In another special embodiment, the monofilaments can be monofilament-like, that is multifilaments at least partially melted.

When more than one filament is used, the filaments may be braided, twisted, enlarged, intertwisted or arranged in some other multifilament configuration or structure. Structures such as tapes or sheets can also comprise one or more monofilaments or multifilaments, optionally (but not preferred) with an adhesive connecting the yarns.

In a preferred embodiment of the present invention the treated HPPE yarn is a monofilament.

In another preferred embodiment of the present invention the treated HPPE yarn is a multifilament. Multifilament encompasses also a monofilament-like structure obtained from a multifilament yarn for example as described in EP 0 740 002 A1.

In another preferred embodiment of the present invention the treated HPPE yarn is a yarn configuration or yarn structure such as for example a braid, a textile, a woven, a non-woven, a knitted, a braided or otherwise formed structure comprising the treated HPPE yarn or consisting of the treated HPPE yarn.

In a preferred embodiment of the present invention the monofilament or multifilament treated HPPE yarn comprises ultra-high molecular weight polyethylene (UHMWPE) filaments. Ultra high molecular weight polyethylene (UHMWPE) is a subset of the thermoplastic polyethylene. UHMWPE is synthesized from monomers of ethylene, which are bonded together forming molecules of polyethylene that are several orders of magnitude longer than untreated high-density polyethylene (HDPE). In general, HDPE molecules have between 700 and 1,800 monomer units per molecule, whereas UHMWPE molecules tend to have 100,000 to 250,000 monomers. The molecular weight of UHMWPE is typically higher than 2 million and usually in the range between 2 to 6 million. UHMWPE is a very tough material, actually being the toughest of all known thermoplastics. UHMWPE is odorless, tasteless, and nontoxic. UHMWPE is processed using for example the following methods: compression molding, ram extrusion, gel spinning, sintering, and kneading. In gel spinning, a precisely-heated gel of UHMWPE is processed by an extruder through a spinneret. The extrudate is drawn through the air and then cooled. The end-result is a yarn with a high degree of molecular orientation, high crystallinity and therefore exceptional tensile strength. Gel spinning depends on isolating individual chain molecules in the solvent so that intermolecular entanglements are minimal. If intermolecular entanglements will not be kept to a minimum, then they are the main responsible for making a material such as UHMWPE unprocessable. In addition intermolecular entanglements can make chain orientation more difficult, lowering the mechanical strength of the final product. When UHMWPE is formed to fibers, the polymer chains can typically attain a parallel orientation greater than 90% for example greater than 95% and a high level of crystallinity for example a crystallinity of up to 85%. Polymerisation of ethylene into UHMWPE was commercialized in the 1950s by Ruhrchemie AG, which changed names over the years; today UHMWPE powder materials are produced by Ticona, Braskem, and Mitsui. UHMWPE is available commercially either as consolidated forms, such as sheets or rods, and as fibers. UHMWPE powder may also be directly molded into the final shape of a product. UHMWPE filaments which can be used herein include those sold under the trade name DYNEEMA which are available from DSM (Heerlen, the Netherlands).

In the context of the present invention, UHMWPE is herein defined as a polyethylene having an intrinsic viscosity ($\eta_{intrinsic}$) of more than 5 dl/g (deciliter per gram). Intrinsic viscosity is a measure for molecular weight that can be more easily determined from parameters such as $M_n$ and $M_w$. The $\eta_{intrinsic}$ determined according to method PTC-179 (Hercules Inc. Rev. Apr. 29, 1982) at 135° C. in decaline, the dissolution time being 16 hours, with DBPC as the anti-oxidant in an amount of 2 g/l (gram per liter) solution, and the viscosity at different concentrations is extrapolated to zero concentration. Because of their long molecule chains, stretched polyolefin fibers with a $\eta_{intrinsic}$ of more than 5 dl/g have very good mechanical properties, such as a high tensile strength, modulus, and energy absorption at break. More preferably, a polyethylene with a $\eta_{intrinsic}$ of more than 10 dl/g is chosen. This is because such gel-spun UHMWPE yarn offers a combination of high strength, low relative density, good hydrolysis resistance, and excellent wear properties, making it particularly suited for use in various biomedical applications, including implants.

Preferably, the UHMWPE of the present invention is a linear polyethylene, i.e. a polyethylene with less than one side chain or branch per 100 carbon atoms, and preferably less than one side chain per 300 carbon atoms, a branch generally containing at least 10 carbon atoms. Preferably, only polyethylene is present, but alternatively the polyethylene may further contain up to 5 mol % of alkenes that may or may not be copolymerized with it, such as propylene, butene, pentene, 4-methylpentene or octene. The polyethylene may further contain additives that are customary for such fibres, such as anti-oxidants, thermal stabilizers, colorants, etc., up to 15% w/w of the total weight of the polyethylene plus the additives, preferably 1-10% w/w of the total weight of the polyethylene plus the additives. The UHMWPE may further be added with a polyethylene with lower molecular weight, preferably up to 10% mol of the total weight of the UHMWPE plus the polyethylene with lower molecular weight.

Monofilament or multifilament HPPE yarns have been described in various publications, including EP 0 205 960 A, EP 0213208 A1, U.S. Pat. No. 4,413,110, WO 01 73173 A1, and Advanced Fiber Spinning Technology, Ed. T. Nakajima, Woodhead Publ. Ltd (1994), ISBN 1-855-73182-7, and references cited therein, all incorporated herein by reference. In these publications, monofilament or multifilament HPPE yarns are made by a gel spinning process. Gel spun monofilament or multifilament HPPE yarns multifilament yarns have favorable mechanical properties, like a high modulus and a high tensile strength.

The diameter of a monofilament HPPE yarn is herein understood to mean the average diameter D of the HPPE yarn calculated from the dtex (g/10 km, grams of yarn per 10 Km of yarn length) of the yarn according to equation 1:

$$D(\mu m) = (4/\pi \cdot \rho^{-1} \cdot dtex \cdot 10^{-7})^{1/2} \cdot 10^6 \quad \text{(equation 1)}$$

wherein density $\rho$ of the monofilament is assumed to be 970 kg/m$^3$.

The treated HPPE yarn according to the present invention has a diameter which is large enough to be used as a surgical suture. Filaments having a high diameter are more robust during handling (for example with regard to friction) by a surgeon and more abrasion resistant. The surgical suture sizes are defined by the United States Pharmacopeia (USP). Nowadays, the USP designations for surgical sutures range from 11-0 (the thinnest surgical sutures) to 7 (the thickest surgical sutures). Exemplary USP designations for surgical sutures of the present invention that can be used as surgical sutures include but are not limited to, USP 11-0 (a yarn having a diameter of about 10 μm), USP 10-0 (a yarn having a diameter of about 20 μm), USP 9-0 (a yarn having a diameter of 30 μm), USP 8-0 (a yarn having a diameter of about 40 μm), USP 7-0 (a yarn having a diameter of about 50 μm), USP 6-0 (a yarn having a diameter of about 70 μm), USP 5-0 (a yarn having a diameter of about 100 μm). The higher diameter provides a higher total strength, although typically the specific strength decreases with a diameter increase. The diameter of the yarn is preferably at most 150 μm (may be used as a surgical suture of USP 4-0 designation), since it is difficult to eliminate the residual spin solvent to the level of 100 ppm or less. More preferably, the diameter of the yarn is at most 100 μm, even more preferably the diameter of the yarn is at most 50 μm, most preferably the diameter of the yarn is at most 40 μm, for example the diameter of the yarn is at most 30 μm. The diameter of the yarn is preferably at least 1 μm, more preferably the diameter of the yarn is at least 2 μm, even more preferably the diameter of the yarn is at least 3 μm, most preferably the diameter of the yarn is at least 5 μm, for example the diameter of the yarn is at least 6 μm.

The treated HPPE yarn according to the present invention which can be used as a surgical suture can also have a diameter higher than USP 4.0. Such sutures with diameter higher than USP 4.0 can be also obtained via a combination of yarns of smaller diameter or via yarns produced by methods such as compression molding, ram extrusion, gel spinning, sintering, and kneading.

In yet another embodiment of the invention, the surgical repair article is a tape or a film, and the HPPE is comprised in the tape or film. The tape or film is here considered a monofilament of HPPE even if the tape or film may have a size and shape much larger than monofilaments typically used in a multifilament HPPE yarn as it is extruded from a melt or solution through one spin hole, which spin hole may be quite large and for example rectangular). Such a tape or film may for example be produced by feeding a polyethylene, preferably an ultra high molecular weight polyethylene, to an extruder, extruding a tape or a film at a temperature above the melting point of HPPE and drawing the extruded polymeric tape or film unidirectionally or biaxially. If desired, prior to feeding the polyethylene to the extruder, the polyethylene may be mixed with a suitable liquid organic compound such as for example decaline or paraffin, for instance to form a solution, a suspension or a gel, such as is preferably the case when using UHMWPE. In one sub-embodiment of this embodiment of the invention, the surgical repair article is a porous membrane, preferably a porous HPPE membrane, which membrane for example may be prepared according to EP 500 173 or EP 504 954 (both incorporated herein by reference) and subsequently coated with a coating comprising a sol/gel as described elsewhere.

Another way for producing tapes or films is via a solid state process comprising the steps of calendaring powdered HPPE at elevated temperature to form a coherent tape or film, followed by stretching the tape or film unidirectionally or biaxially.

In another embodiment, the present invention provides for the treated HPPE yarn, wherein the diameter of the treated HPPE yarn is less than 50 μm, preferably less than 30 μm.

In another embodiment of the present invention, the treated HPPE yarn of the present invention has a diameter of about 10 to 17 μm, which can be used as a suture of USP 10-0.

In yet another embodiment of the present invention, the treated HPPE yarn of the present invention, has a diameter of about 11 to 15 μm, which can be used as a suture of USP 10-0.

In an additional embodiment of the present invention, the treated HPPE yarn of the present invention is large enough and can have a diameter of up to 5 mm to be used as a medical cable.

In yet another embodiment of the present invention, the treated HPPE yarn is configured to a mesh suitable for medical applications such as a medical mesh for example a hernia mesh.

In another embodiment of the present invention, an untreated HPPE yarn is configured to a mesh suitable for medical applications such as a medical mesh for example a hernia mesh and subsequently the mesh is subject to the deposition of a porous polyolefin layer that adheres to the surface of the medical mesh and covers at least partly the surface of the medical mesh; and the deposition of a composition comprising an active agent and which composition is at least partially absorbed within the porous polyolefin layer.

The residual spin solvent is herein understood to mean the content of the solvent used in making the monofilament, which is still remaining in the final monofilament. In the process of making the yarn, any of the known solvents for gel spinning of UHMWPE can be used. Suitable examples of spinning solvents include aliphatic and alicyclic hydrocarbons, e.g. octane, nonane, decane and paraffins, including isomers thereof; petroleum fractions; mineral oil; kerosene; aromatic hydrocarbons, e.g. toluene, xylene, and naphthalene, including hydrogenated derivatives thereof, e.g. decalin and tetralin; halogenated hydrocarbons, e.g. monochlorobenzene; and cycloalkanes or cycloalkenes, e.g. careen, fluorine, camphene, menthane, dipentene, naphthalene, acenaphtalene, methylcyclopentandien, tricyclodecane, 1,2,4,5-tetramethyl-1,4-cyclohexadiene, fluorenone, naphtindane, tetramethyl-p-benzodiquinone, ethylfuorene, fluoranthene and naphthenone. Also combinations of the above-enumerated spinning solvents may be used for gel spinning of monofilament or multifilament HPPE yarns, the combination of solvents being also referred to for simplicity as spinning solvent. In one embodiment, the spinning solvent of choice has a low vapor pressure at room temperature (23° C.), e.g. paraffin oil. It was also found that the process of the invention is especially advantageous for relatively volatile spinning solvents at room temperature, as for example decalin, tetralin and kerosene grades. Most preferably, the spinning solvent is decalin.

The combination of the large diameter and the low spin solvent residue makes the monofilament highly suitable for use in medical applications.

The diameter of 30 μm or more allows the monofilament to be used as a yarn without further twisting or fusing process, with an advantage that there is less possibility of bacteria harboring in pores.

The residual spin solvent content of 100 ppm or less makes the cumbersome cleaning process unnecessary for use in most medical applications. Preferably, the residual solvent content is 80 ppm or less and even more preferably, 60 ppm or less. The lower solvent content makes the monofilament yarn even more suitable for some special medical applications.

In an embodiment of the present invention, the treated HPPE yarn has a tenacity of 15 cN/dtex or more. Such tenacity is suitable for use in a mesh. In applications where especially high tenacity is required, such as a suture, the yarn preferably has a tenacity of 25 cN/dtex or more.

Therefore, a treated HPPE yarn comprising UHMWPE is provided having a diameter of 6 μm or more and a spin solvent residue of less than 100 ppm, wherein the yarn is a monofilament. The solution of UHMWPE in a solvent is spun from a spin plate comprising one spin hole or a plurality of spin holes. Preferably, the spinning of the filament is done in a manner in which the flow rate of the solution to be spun is controlled. In one embodiment, the solution of UHMWPE is spun from a spin plate comprising a flow rate control means present before the spin hole. The flow rate control means may be a metering pump. In an embodiment wherein the spin plate comprises a plurality of flow rate control means associated with different spin holes, each of the flow rate control means preferably controls the flow rate from the respective spin holes individually. Alternatively, the plurality of flow rate control means may also control the flow rate from different spin holes in the same manner.

The control of the solution flow rate is especially advantageous in this invention, since the effect of an inconstant flow rate is larger in making a larger diameter filament. A large diameter of the spin hole gives a higher possibility that the filament has a variation in its properties over its diameter. This will result in a more homogeneous monofilament.

The monofilament which forms the present yarn has a diameter large enough for use as a yarn in medical applications, e.g. as a surgical suture, from handling perspective and mechanical properties. The monofilament thus does not need to be twisted to make a yarn as in multifilaments, hence reducing the required number of steps and providing a simplified method of making a yarn. Furthermore, the closed structure of the monofilament has no space for attracting bacteria.

When more than one filament is used, the filaments may be braided, twisted, enlarged, intertwisted or arranged in some other multifilament configuration. A particularly useful braid structure for surgical sutures, is the spiroid braid structure described in U.S. Pat. No. 5,019,093 and U.S. Pat. No. 5,059,213.

In one embodiment, the treated HPPE yarn or yarn structure or yarn configuration such as a braid, a textile, a woven, a non-woven, a knitted, a braided or otherwise formed structure comprising the treated HPPE yarn or consisting of the treated HPPE, can be combined with untreated HPPE yarn or yarn structure or yarn configuration such as a braid, a textile, a woven, a non-woven, a knitted, a braided or otherwise formed structure comprising the untreated HPPE yarn or consisting of the untreated HPPE, and/or other type of yarn or yarn structure or yarn configuration such as a braid, a textile, a woven, a non-woven, a knitted, a braided or otherwise formed structure comprising the other type of yarn or consisting of the other type of yarn. Preferably, the other type of yarn or yarn structure or yarn configuration such as a braid, a textile, a woven, a non-woven, a knitted, a braided or otherwise formed structure comprising the other type of yarn or consisting of the other type of yarn, is a high-performance one such as for example nylon yarns, teflon yarns, polypropylene yarns, etc.

In another aspect the present invention provides for a method for making a treated HPPE yarn, comprising the steps of:
depositing via simultaneous plasma polymerisation and plasma etching, a porous polyolefin layer that adheres to a surface of a HPPE yarn and covers at least partly the surface of the HPPE yarn; a pre-treated HPPE yarn is thus prepared;
depositing a composition comprising an active agent, preferably the composition also comprising a lipid and/or an alkyd to the pre-treated HPPE yarn at an effective temperature and for an effective time; a treated HPPE yarn is thus prepared;
optionally using the thus prepared treated HPPE yarn to prepare a yarn structure or yarn configuration such as a braid, a textile, a woven, a non-woven, a knitted, a braided or otherwise formed structure comprising the treated HPPE yarn or consisting of the treated HPPE yarn.

In yet another embodiment, the present invention provides for the treated HPPE yarn obtainable by the method for making the treated HPPE yarn as described herein above.

Plasma polymerization uses plasma sources to generate a gas discharge that provides energy to activate or fragment gaseous or liquid monomer, often containing a vinyl group, in order to initiate polymerization. Plasma polymerization can be used to deposit polymer thin films. By selecting the monomer type and the energy density per monomer, known as Yasuda parameter, the chemical composition and structure of the resulting thin film can be varied in a wide range. In the context of the present invention, preferably the plasma polymerization takes place under vacuum and in that case it would be called vacuum plasma polymerization. The use of appropriate plasma gases (including gaseous alkene monomers) and plasma operating conditions during plasma polymerization can produce a HPPE yarn having a polyolefin layer on its surface. The plasma polymerization may be based on specific sequences of inert gases preferably noble gases, and alkene monomers which are used in the present invention to form upon plasma polymerization, the polyolefin layer. The gases should be capable of creating plasma and the polymerization of the alkene monomer(s) starts once the plasma is generated.

Plasma etching is a form of plasma processing and it involves a high-speed stream of plasma of an appropriate gas mixture being shot (in pulses) at a sample. The plasma source, known as etch species, can be either charged (ions) or neutral (atoms and radicals). During the process, the plasma will generate volatile etch products at room temperature from the chemical reactions between the elements of the material etched and the reactive species generated by the plasma. Eventually the atoms of the shot element embed themselves at or just below the surface of the target, thus modifying the physical properties of the target. Plasma systems ionize a variety of source gases in a vacuum system by using RF excitations. The frequency of operation of the RF power source is frequently 13.56 MHz, chosen by the Federal Communications Commission (FCC) for industrial and scientific use. Nevertheless, it can be used at lower frequencies (kilohertz) or higher (microwave). The mode of operation of the plasma system will change if the operating pressure changes. Also, it is different for different structures of the reaction chamber. In the simple case, the electrode structure is symmetrical, and the sample is placed upon the grounded electrode. For example, free radicals such as fluorine or chlorine can be created in the plasma and react at the sample surface. Without the assistance of the plasma, much higher temperature would be required. The low processing temperature is possible because the plasma generates atoms, molecular radicals and positive ions that are more chemically reactive than the normal molecular gases from which the species are created. Exemplary gases are but not limited to carbon dioxide, carbon monoxide, ammonia, chlorine ($Cl_2$), halocarbons such as for example $CF_4$, $CF_3Br$ and $CF_2Cl_2$ etc., HCl, $SF_6$, etc. In the context of the present invention, preferably the gas used in the plasma etching is selected from the group consisting of carbon dioxide ($CO_2$) and ammonia ($NH_3$).

The simultaneous plasma polymerization and plasma etching can also take place in conjunction with a dynamic masking process, the latter resulting in a porous polyolefin layer that adheres to the surface of a HPPE yarn and covers selectively the surface of a HPPE yarn. By using this technique one may latter on selectively deposit a composition comprising an active agent to specific locations on the surface of HPPE yarn, which locations will offer mechanical stability to the composition thus enhancing its long-term effects.

It was found that by combining in one single process step, (vacuum) plasma polymerisation of for example ethylene (monomer for the plasma polymerization) which is a gas and plasma etching to create a pre-treated HPPE yarn, allows reaching a relatively low total coating layer thickness. Although the relative thickness of the coating with respect to the dimensions of the structural member and/or the HPPE filaments may be varied between wide limits, preferred is a relatively low coating layer thickness. If the coating layer is too thick in relation to the structural member and/or the HPPE filaments, the flexibility of the member and/or the filaments becomes too low, but this will generally be dependent on the use of, and the size or dimensions of the member and/or the filaments. Very thick coatings may for example be advantageous when the surgical repair product comprises thick monofilament or monofilament-like yarn for example having a diameter of about 50 to 250 µm. In this case thick coatings having a thickness of for example 100 nm to 10 µm may be advantageous. Such thick coatings have the advantage that very high loadings of biologically active compound may be achieved as well as very large molecules, such as for example growth factors, antibiotics, etc, easily may be incorporated in the coating.

In a preferred embodiment, the present invention provides for a treated HPPE yarn comprising a porous polyolefin layer that adheres to a surface of a HPPE yarn and covers at least partly the surface of the HPPE yarn, wherein the porous polyolefin layer is deposited to the HPPE yarn via simultaneous plasma polymerization and plasma etching.

In the context of the present invention, the thickness of the porous polyolefin layer depends on the time the plasma polymerization and plasma etching will take place. The thickness of the porous polyolefin layer of the present invention is at least 5 nm, preferably at least 10 nm, more preferably at least 15 nm, most preferably at least 18 nm, for example at least 20 nm. The thickness of the porous polyolefin layer is at most 1000 nm, preferably at most 500 nm, more preferably at most 400 nm, most preferably at most 300 nm, for example at most 250 nm.

It was surprisingly found that the presence of the porous polyolefin layer in the present invention provides not only enhanced adhesion of the composition to an untreated HPPE yarn but at the same time contributes to an enhanced control release of an active agent. Moreover, it was surprisingly found that the presence of the porous polyolefin layer did not deteriorate the mechanical properties of the treated HPPE yarns substantially, since the treated HPPE yarns according to the invention have at least comparable mechanical properties in respect to the mechanical properties of untreated HPPE yarns.

The deposition of an active agent to a HPPE yarn comprising the porous polyolefin layer can take place via various ways such as for example dip-coating, spin coating, etc. The effective time and temperature for the deposition of an active agent to a pre-treated HPPE yarn can be derived upon routine experimentation by the skilled person. Preferably the deposition of an active agent to a pre-treated HPPE yarn takes place via dip-coating.

Dip-coating refers to the immersing of a substrate into a tank containing a coating material, removing the piece from the tank, and optionally allowing it to drain. The coated piece can then be dried by force-drying or baking. It is a popular way of creating thin film coated materials along with the spin coating procedure. The dip coating process can, generally, be separated into three stages:
a) Immersion: the substrate is immersed in the solution of the coating material at a constant speed preferably judder free;
b) Dwell time: the substrate remains fully immersed and motionless to allow for the coating material to apply itself to the substrate;
c) Withdrawal: the substrate is withdrawn, again at a constant speed to avoid any judders. The faster the substrate is withdrawn from the tank the thicker the coating material that will be applied to the board.

The effective time and temperature for all the above steps of the dip-coating process that are the preferred time and temperature conditions for the dip-coating process steps, are selected such that the HPPE filaments of the structural member will not soften or start to melt, so that they do not loose their molecular orientation. Residence times during which the HPPE yarn comprising the porous polyolefin layer and coating are exposed to a certain temperature are preferably at least 10 seconds, more preferably at least 12 seconds, even more preferably at least 15 seconds, most preferably at least 20 seconds, for example at least 25 seconds. Residence times during which the HPPE yarn comprising the porous polyolefin layer and coating are exposed to a certain temperature are preferably at most 60 minutes, more preferably at most 45 minutes, even more preferably at most 30 minutes, most preferably at most 20 minutes, for example at most 15 minutes. Preferably, the temperatures that can be used in any of the process steps of the dip-coating should be selected such that the HPPE filaments of the structural member will not soften or start to melt, so that they do not loose their molecular orientation and at the same time the coating material such as for a example a solution of an active agent in a solvent is in liquid form. More preferably, the temperatures applied can be at least 10° C., even more preferably at least 15° C., most preferably at least 20° C., for example at least room temperature. Preferably, the temperatures applied can be at most 90° C., even more preferably at most 80° C., most preferably at most 70° C., for example at most 60° C. By routine experimentation, the skilled man can find favourable time and temperature settings that suit on one hand the physical/chemical properties of the materials involved and on the other hand the intended application. Drying of the coating material, preferably after step c) of the dip-coating process, can be performed by heat treatment according to a number of methods. Drying by ambient heat (equivalent to drying at room temperature), vacuum drying, electromagnetic drying, acoustic drying, spray-drying or freeze-drying may all be used. In a preferred embodiment of the method, the heat treatment temperature is below 120° C., more preferably below 100° C., even more preferably below 80° C., most preferably below 50° C., for example room temperature. These preferred temperature conditions are selected such that the HPPE filaments of the structural member will not soften or start to melt, so that they do not loose their molecular orientation. Residence times during which the precursor structural member and coating are exposed to the oven temperature are for example within the range from about 30 seconds to about 15 min. The skilled man can find favourable settings by routine experimentation.

In another embodiment the present invention provides for the method for making the treated HPPE yarn of the present invention and which method is described herein, wherein the simultaneous plasma polymerisation and plasma etching is carried out in the presence of the HPPE yarn, an alkene gas, preferably ethylene or mixture of alkene gases, an inert gas, preferably a noble gas preferably argon or mixture of inert gases; and either carbon dioxide ($CO_2$) or ammonia ($NH_3$).

In another embodiment, the present invention provides for a the method for making the treated HPPE yarn of the present invention and which method is described herein, wherein the HPPE yarn is converted into a yarn structure or yarn configuration such as a braid, a textile, a woven, a non-woven, a knitted, a braided or otherwise formed structure comprising the HPPE yarn prior to the step of depositing the composition comprising the active agent, preferably the HPPE yarn is converted into the yarn structure or yarn configuration prior to the step of depositing the composition comprising the active agent and prior to the step of depositing the porous polyolefin layer.

The addition at a particular time, say at a time of one's choose, of the composition comprising the active agent that may preferably comprise a lipid and/or an alkyd to a pre-treated HPPE yarn according to the present invention has the benefit that chemically and/or physically unstable active agents otherwise difficult to store for prolonged time periods in the form of a treated HPPE yarn, can be used since they can be added at the time of application of the treated HPPE yarn.

The same benefit applies for any yarn structure or yarn configuration comprising or consisting of the pre-treated HPPE yarn or yarn structure or yarn configuration, according to the present invention.

In another embodiment the present invention provides for the method for making a treated HPPE yarn or yarn structure or yarn configuration as described herein, wherein the simultaneous plasma polymerisation and plasma etching is carried out in the presence of the HPPE yarn, an alkene gas, preferably ethylene or mixture of alkene gases, an inert gas, preferably a noble gas preferably argon or mixture of inert gases; and either carbon dioxide ($CO_2$) or ammonia ($NH_3$).

In a preferred embodiment, the invention provides for the treated HPPE yarn, treated HPPE yarn structure or treated HPPE yarn configuration such as a braid, a textile, a woven, a non-woven, a knitted, a braided or otherwise formed structure comprising the HPPE yarn or consisting of the HPPE yarn, to be obtained by any of the processes as described herein.

In a preferred embodiment, the invention provides for the treated HPPE yarn, treated HPPE yarn structure or treated HPPE yarn configuration such as a braid, a textile, a woven, a non-woven, a knitted, a braided or otherwise formed structure comprising a HPPE yarn or consisting of HPPE yarn, obtainable by the process as described herein above.

The active agent can be a flavour agent, a pigment, a dye, a colorant, an insect repellent, a UV-Vis absorber, a colorant, a scent compound, a catalyst, a photo-/UV-stabilizer, a flame retardant, a bioactive compound such as a fungicide, an insecticide, an antiviral, a growth factor, a growth factor inhibitor, a growth factor receptor, a bone inductive agent, or a complete or partial functional gene, anti-inflammatory agents, anti-infective agents (e.g. antibiotics and antiviral agents), antimicrobial agents, anticancer agents, antilipidemic agents, analgesics and analgesic combinations, anti-asthmatic agents, anticonvulsants, antidepressants, anti-diabetic agents, and agents used for other diseases, etc. Typically, the molecular weight of the active agent is lower than about 3000 g/mol (grams per mol), preferably lower than 2000 g/mol, even more preferably lower than 1500 g/mol, most preferably lower than 1200 g/mol, for example lower than 1000 g/mol. Desirably, the structure of the active agent is such as to facilitate its penetration through the porous polyolefin layer. Exemplary active agents include, but are not limited to drugs, prodrugs, neurotropic agents, antilipidemic agents, antimicrobial agents, fungicides, anticonvulsants, steroids, hormones, anti-inflammatory agents, anticancer agents, antibiotics, photosensitizers, flame retardants, UV-stabilizers, radical initiators, dyes, lubricants, etc. The active compound can comprise a mixture of the same and/or of distinct compounds described above. The active compound preferably comprises a mixture of four, even more preferably comprises a mixture of three, most preferably comprises a mixture two, for example the active compound comprises one of the above compounds.

In the context of the present invention the biologically active agent can be any organic, inorganic or living agent that is biologically active. Preferably, the biologically active agent is an organic or inorganic compound. Suitable biologically active agents include proteins, polypeptides, polysaccharides (e.g. heparin), oligosaccharides, mono- or disaccharides, organometallic compounds other organic compounds or inorganic compounds. It can also be a living or dead cell, a bacterium, an hormone, a virus or a part thereof. Exemplary bioactive compounds include, but are not limited to fungicides (amphotericin B, nystatin, other polyene antibiotics, etc), insecticides, antivirals, growth factors, growth factor inhibitors, growth factor receptors, bone inductive agents (hydroxylapatite, beta-tricalciumphosphate, etc.) or complete or partial functional genes, anti-inflammatory agents, anti-infective agents (e.g. antibiotics and antiviral agents), antimicrobial agents, anticancer agents (paclitalex, tamoxifen, doxorubicin, geldanamycin, photosensitizers, daunomycin etc.), antilipidemic agents, analgesics and analgesic combinations, anti-asthmatic agents, anticonvulsants, antidepressants, anti-diabetic agents, and agents used for other diseases, etc.

In a special embodiment the present invention provides for a treated HPPE yarn, wherein the active agent comprises a bioactive compound, preferably an antimicrobial agent. An antimicrobial agent is a substance that kills or inhibits the growth of microorganisms such as bacteria, fungi, or protozoans, as well as destroying viruses. Antimicrobial agents either kill microbes (microbicidal) or prevent the growth of microbes (microbistatic). In tissue ligation for instance, the incorporation of an antimicrobial agent will help to avoid infections and therefore promote healing.

In an additional embodiment the present invention provides for a treated HPPE yarn, wherein the active agent is an antimicrobial agent, preferably triclosan.

In another embodiment the present invention provides for a treated HPPE yarn wherein the active agent is an antimicrobial agent.

In a special embodiment the present invention provides for a treated HPPE yarn wherein the active agent is triclosan.

In yet another special embodiment the present invention provides for a treated HPPE yarn wherein the active agent comprises a bioactive compound preferably a fungicide. Fungicides are chemical compounds or biological organisms used to kill or inhibit fungi or fungal spores.

In another special embodiment the present invention provides for a treated HPPE yarn wherein the active agent comprises a bioactive compound preferably an antimicrobial and/or a fungicide together with a growth factor. A growth factor is a naturally occurring substance capable of stimulating cellular growth, proliferation and cellular differentiation. Usually it is a protein or a steroid hormone. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis).

In another embodiment of the present invention, the present invention provides for a treated HPPE yarn wherein the active agent comprises a bioactive compound preferably a bone inductive agent. Exemplary bone inductive agents but limited to are hydroxylapatite, beta-tricalciumphosphate. The treated HPPE yarns comprising a bone inductive agent can contribute to faster healing of soft tissue and/or bone and can enhance ligation between the treated HPPE yarn or yarn structure or yarn configuration and soft tissue and/or bone.

In yet another embodiment of the present invention, the present invention provides for a treated HPPE yarn wherein the active agent is selected from the group consisting of hydroxylapatite, beta-tricalciumphosphate or mixtures thereof.

In another embodiment of the present invention, the treated HPPE yarn of the invention further comprises a growth factor.

In yet another embodiment of the present invention, the treated HPPE yarn of the invention further comprises a growth factor which growth factor is selected from the group consisting of bone morphogenetic proteins (BMP) and vascular endothelial growth factors.

In a further special embodiment the present invention provides for a treated HPPE yarn, wherein the active agent comprises a UV-Vis-absorber. UV-Vis-absorbers are substances that dissipate the absorbed light energy from UV or visible rays, usually as heat. This reduces the absorption of UV or visible rays by a material such as for example a polymer or polymer matrix and hence reduces the rate of weathering this material. Typical UV-Vis absorbers are oxanilides for polyamides, benzophenones, benzotriazoles and hydroxyphenyltriazines, etc.

In a further special embodiment the present invention provides for a treated HPPE yarn, wherein the active agent comprises a photo-/UV-stabilizer. Photo-/UV-stabilizers are substances that are able to prevent effects such as oxidation, chain scission, uncontrolled recombinations and cross-linking reactions that are caused by photo-/UV-oxidation of a material susceptible to photo-/UV-oxidation such as for example certain classes of polymers. Exemplary photo-/UV-stabilizers include but are not limited to hindered amine light stabilizers, etc.

In a further special embodiment the present invention provides for a treated HPPE yarn, wherein the active agent comprises a flame retardant. Flame retardants are substances that inhibit or resist the spread of fire. Exemplary flame retardants include but are not limited to minerals such as asbestos, compounds such as aluminium hydroxide, magnesium hydroxide, hydromagnesite, antimony trioxide, various hydrates, red phosphorus, boron compounds mostly borates, tetrakis(hydroxymethyl)phosphonium salts, mineral acids such as hydrochloric acid, synthetic materials, usually halocarbons such as organochlorines for example polychlorinated biphenyls (PCBs), chlorendic acid derivates (most often dibutyl chlorendate and dimethyl chlorendate), chlorinated paraffins; organobromines for example polybrominated diphenyl ether (PBDEs), pentabromodiphenyl ether (pentaBDE), octabromodiphenyl ether (octaBDE), decabromodiphenyl ether (decaBDE) and hexabromocyclododecane (HBCD); organophosphates in the form of halogenated phosphorus compounds for example tri-o-cresyl phosphate, tris(2,3-dibromopropyl) phosphate (TRIS), bis(2,3-dibromopropyl) phosphate, tris(1-aziridinyl)-phosphine oxide (TEPA), and others.

In another special embodiment the present invention provides for a treated HPPE yarn, wherein the active agent comprises a dye.

In yet another special embodiment the present invention provides for a treated HPPE yarn, wherein the active agent comprises a catalyst.

In yet another special embodiment the present invention provides for a treated HPPE yarn, wherein the active agent comprises a colorant.

The active agent can be added to a pre-treated HPPE yarn by various ways. The active agent can be deposited to a pre-treated HPPE yarn as neat substance or upon been previously mixed with a solid or liquid or gaseous substance-carrier such as for example a solvent e.g. water, ethyl acetate, ethanol, methanol, acetonitrile, etc., or an inert gas e.g. nitrogen, helium, argon, etc., or a powder, or mixtures thereof. The deposit of the active agent to the pre-treated HPPE yarn can be done via a variety of ways known to the skilled person such as for example spraying, flame spraying, fluidized bed process, spin coating, dip-coating. Preferably, the active is deposited to a pre-treated HPPE yarn by dip-coating as the latter has been explained herein. In the context of the present invention and according to the description of the dip-coating process, the substrate is the pre-treated HPPE yarn, the coating material can be a solution of the active agent in a organic or inorganic solvent such as for example water, ethyl acetate, ethanol, methanol, acetonitrile, etc., and the coated piece is the treated HPPE yarn. Preferably, the coating material is a solution of the active agent in an organic solvent, more preferably the coating material is a solution of the active agent in ethyl acetate.

The amount of the active agent in the treated HPPE yarn depends mainly on the type of the intended end-application and the intensity the specific action or effect attributed to the active agent is intended to be expressed once the active agent becomes part of a treated HPPE yarn. The skilled person in the art knows the amounts he can use the active agent in respect to the end-application and the effect he wishes to achieve.

In a preferred embodiment the present invention provides for a treated HPPE yarn, wherein the active agent is added to an organic solvent.

In another preferred embodiment the present invention provides for a treated HPPE yarn, wherein the active agent is added to a solution of a lipid in an organic solvent.

In yet another preferred embodiment the present invention provides for a treated HPPE yarn, wherein the active agent is added to an oxidizing alkyd.

In another embodiment of the present invention, the treated HPPE yarn of the invention also comprises a lipid.

Lipids are a broad group of naturally-occurring molecules which includes fats, fatty acids, oils, waxes, sterols, fat-soluble vitamins (such as vitamins A, D, E and K), monoglycerides, diglycerides, phospholipids, glycolipids and others.

Although the term lipid is sometimes used as a synonym for fats, fats are a sub-group of lipids called triglycerides. Lipids also encompass molecules such as fatty acids and their derivatives (including tri-, di-, and monoglycerides and phospholipids), as well as other sterol-containing metabolites such as cholesterol.

Triglyceride (more properly known as triacylglycerol, TAG or triacylglyceride) is a glyceride in which the glycerol is esterified with three fatty acids. It is the main constituent of vegetable oil and animal fats. Triglycerides are formed from a single molecule of glycerol, combined with three fatty acids on each of the OH groups, and make up most of fats digested by humans. Ester bonds form between each fatty acid and the glycerol molecule. Triglycerides can be saturated or unsaturated. The general chemical formula of a triglyceride is RCOO—$CH_2CH$(—OOCR')$CH_2$—OOCR", where R, R', and R" are long alkyl chains. The three fatty acids RCOOH, R'COOH and R"COOH can be all different, all the same, or only two the same.

The oils are mixtures of triglycerides with different fatty acids distributed among the triglyceride molecules. Exemplary oils but not limited to are linseed oil, sunflower oil, soybean oil, safflower oil, tung oil, castor oil, cocunut oil, palm oil, tall oil fatty acids (TOFA), etc. Compositions of the oils vary, sometimes quite widely, with variations in plant strain, climate, soil, and other growth factors. Animal oils and fats are also triglycerides and can be used in the context of the present invention. Preferably, animal oils are to be used for example refined fish oils. Oils containing conjugated carbon double bonds are called conjugated oils. A conjugated oil is an oil which contains carbon atoms which are covalently bond with alternating single and double bonds e.g., —C═C—C═C—C—. Oils containing non-conjugated carbon double bonds are called non-conjugated oils. Some oils are drying oils. A drying oil is an oil that hardens to a tough, solid film after a period of exposure to air. The term "drying" is actually a misnomer—the oil does not harden through the evaporation of water or other solvents, but through a chemical reaction in which the components crosslink by the action of oxygen. The reactivity of drying oils with oxygen results from the presence of diallylic groups which are chemical groups consisting of two carbon double bonds separated by methylene groups, i.e. —CH═$CHCH_2CH$═CH—, or conjugated double bonds. Drying, semidrying and non-drying oils are often defined based on their iodine value that is grams of iodine required to saturated the double bonds of 100 g of an oil. According to it drying oils are those oils with iodine value higher than 140; semidrying oils are those oils with iodine value in the range of 125-140; and non-drying oils have iodine values lower than 125. The reactions taking place during drying are complex and result in crosslinked films. The drying of oils can be catalyzed by the use of oil soluble dryers such as oil-soluble metal salts or mixtures thereof, for example oil-soluble cobalt, manganese, lead, zirconium, calcium salts, etc. Several types of chemical modification of oils, especially drying oils can be practiced. These chemical modifications result in drying oil modified alkyds, epoxy esters, uralkyds, maleated oils, vinyl modified oils, varnishes, esters of higher functionality polyols, etc. In some cases such as for example in the case of esters of higher functionality polyols the drying rate and/or drying time and/or crosslink density of the dried oil are enhanced.

In a special embodiment of the present invention, the treated HPPE yarn comprises an oil.

In yet another special embodiment of the present invention, the treated HPPE yarn comprises a dried oil, which is an oil that has been subject to drying and has formed a crosslinked network. A treated HPPE yarn comprising a dried oil can present enhanced mechanical stability of the composition of the treated HPPE yarn and/or enhanced coatability of the treated HPPE yarn and/or enhanced control over the release of the active agent.

Phospholipids are a class of lipids and are a major component of all cell membranes. Most phospholipids contain a diglyceride, a phosphate group, and a simple organic molecule such as choline; one exception to this rule is sphingomyelin, which is derived from sphingosine instead of glycerol. Glycerol phospholipids contain two fatty acids joined to glycerol. The fatty acids may be different from each other. The third carbon of glycerol is joined to a phosphate group (forming phosphatidic acid), which in turn is frequently joined to another small polar molecule (forming phosphatidylethanolamine, phosphatidylcholine, phosphatidylserine, or phosphatidylinositol). In sphingomyelin, two hydrocarbon chains are bound to a polar head group formed from serine instead of glycerol.

Glycolipids are a class of lipids and are carbohydrate-attached lipids and can be saturated or unsaturated. The general structure of a glycolipid is depicted below.

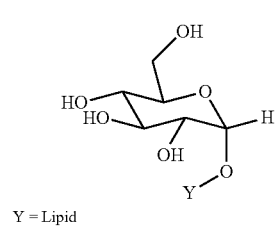

Y = Lipid

Fatty acids are another class of lipids and a preferred class of lipids in the context of the present invention. A fatty acid is a carboxylic acid often with a long unbranched aliphatic tail (chain), which is either saturated or unsaturated. Carboxylic acids as short as butyric acid (4 carbon atoms) are considered to be fatty acids, whereas fatty acids derived from natural fats and oils may be assumed to have at least eight carbon atoms, caprylic acid (octanoic acid). The most abundant natural fatty acids have an even number of carbon atoms because their biosynthesis involves acetyl-CoA, a coenzyme carrying a two-carbon-atom group. Fatty acids are produced by the hydrolysis of the ester linkages in a fat or biological oil (both of which are triglycerides), with the removal of glycerol. Fatty acids are aliphatic monocarboxylic acids derived from, or contained in esterified form in an animal or vegetable fat, oil, or wax. Natural fatty acids commonly have a chain of 4 to 28 carbons (usually unbranched and even numbered), which may be saturated or unsaturated. Fatty acids can be saturated and unsaturated, depending on double bonds. They differ in length as well. Unsaturated fatty acids are of similar form, except that one or more alkenyl functional groups exist along the chain, with each alkene substituting a single-bonded "—$CH_2$—$CH_2$—" part of the chain with a double-bonded "—CH=CH—" portion (that is, a carbon double-bonded to another carbon). The two next carbon atoms in the chain that are bound to either side of the double bond can occur in a cis or trans configuration.

A cis configuration means that adjacent hydrogen atoms are on the same side of the double bond. The rigidity of the double bond freezes its conformation and, in the case of the cis isomer, causes the chain to bend and restricts the conformational freedom of the fatty acid. The more double bonds the chain has in the cis configuration, the less flexibility it has. When a chain has many cis bonds, it becomes quite curved in its most accessible conformations. For example, oleic acid, with one double bond, has a "kink" in it, whereas linoleic acid, with two double bonds, has a more pronounced bend. Alpha-alpha-linolenic acid, with three double bonds, favors a hooked shape. The effect of this is that, in restricted environments, such as when fatty acids are part of a phospholipid in a lipid bilayer, or triglycerides in lipid droplets, cis bonds limit the ability of fatty acids to be closely packed, and therefore could affect the melting temperature of the membrane or of the fat.

A trans configuration, by contrast, means that the next two hydrogen atoms are bound to opposite sides of the double bond. As a result, they do not cause the chain to bend much, and their shape is similar to straight saturated fatty acids. In most naturally-occurring unsaturated fatty acids, each double bond has three n carbon atoms after it, for some n, and all are cis bonds. Most fatty acids in the trans configuration (trans fats) are not found in nature and are the result of human processing (e.g., hydrogenation). A trans fatty acid (commonly shortened to trans fat) is an unsaturated fatty acid molecule that contains a trans double bond between carbon atoms, which makes the molecule less 'kinked' in comparison to fatty acids with cis double bonds. These bonds are characteristically produced during industrial hydrogenation of plant oils.

In addition to saturation, fatty acids are short, medium, or long. Short chain fatty acids (SOFA) are fatty acids with fewer than 6 carbons in their chemical structure. Medium chain fatty acids (MCFA) are fatty acids with 6-12 carbons in their chemical structure, which can form medium chain triglycerides. Long chain fatty acids (LCFA) are fatty acids with more 12-21 carbons in their chemical structures. Very long chain fatty acids (VLCFA) are fatty acids with more than 22 carbons in their chemical structures. In the present invention, the fatty acids have preferably at least 6 carbons in their chemical structure, more preferably have at least 8 carbon atoms, even more preferably have at least 10 carbon atoms, most preferably have at least 12 carbon atoms, for example have at least 14 carbon atoms in their chemical structure. In the present invention, the fatty acids have preferably at most 100 carbons in their chemical structure, more preferably have at most 80 carbon atoms, even more preferably have at most 60 carbon atoms, most preferably have at most 40 carbon atoms, for example have at most 30 carbon atoms in their chemical structure.

Short chain carboxylic acids such as formic acid and acetic acid are miscible with water and dissociate to form reasonably strong acids ($pK_a$ 3.77 and 4.76, respectively). Longer-chain fatty acids do not show a great change in $pK_a$. Nonanoic acid, for example, has a $pK_a$ of 4.96. The significance of their $pK_a$ values therefore has relevance only to the types of reactions in which they can take part. Even those fatty acids that are insoluble in water will dissolve in warm ethanol, and can for example be titrated with sodium hydroxide solution using phenolphthalein as an indicator to a pale-pink endpoint. This analysis is used to determine the free fatty acid content of fats; i.e., the proportion of the triglycerides that have been hydrolyzed.

Fatty acids can be bound or attached to other molecules, such as in triglycerides or phospholipids. Fatty acids react just like any other carboxylic acid, which means they can undergo esterification and acid-base reactions. Reduction of fatty acids yields fatty alcohols. Unsaturated fatty acids can also undergo addition reactions, most commonly hydrogenation, which is used to convert vegetable oils into margarine. With partial hydrogenation, unsaturated fatty acids can be isomerized from cis to trans configuration. Fatty acids at room temperature undergo a chemical change known as auto-oxidation. The fatty acid breaks down into hydrocarbons, ketones, aldehydes, and smaller amounts of epoxides and alcohols. Heavy metals present at low levels in fats and oils promote auto-oxidation. Fats and oils often are treated with chelating agents such as citric acid.

Exemplary fatty acids include but are not limited to, myristoleic acid [$CH_3(CH_2)_3CH=CH(CH_2)_7COOH$], palmitoleic acid [$CH_3(CH_2)_5CH=CH(CH_2)_7COOH$], oleic acid [$CH_3(CH_2)_7CH=CH(CH_2)_7COOH$], linoleic acid [$CH_3(CH_2)_4CH=CHCH_2CH=CH(CH_2)_7COOH$], linolenic acid [$CH_3CH_2CH=CHCH_2CH=CHCH_2CH=CH(CH_2)_7COOH$], pinolenic acid [$CH_3(CH_2)_4CH=CHCH_2CH=CHCH_2CH_2CH=CH(CH_2)_3COOH$], palmitic acid [$CH_3(CH_2)_{14}COOH$], oleic acid [$CH_3(CH_2)_7CH=CH(CH_2)_7COOH$], α-alpha-linolenic acid [$CH_3CH_2CH=CHCH_2CH=CHCH_2CH=CH(CH_2)_7COOH$], arachidonic acid [$CH_3(CH_2)_4CH=CHCH_2CH=CHCH_2CH=CHCH_2CH=CH(CH_2)_3COOH$], eicosapentaenoic acid [$CH_3CH_2CH=CHCH_2CH=CHCH_2CH=CHCH_2CH=CHCH_2CH=CH(CH_2)_3COOH$], erucic acid [$CH_3(CH_2)_7CH=CH(CH_2)_{11}COOH$], docosahexaenoic acid [$CH_3CH_2CH=CHCH_2CH=CHCH_2CH=CHCH_2CH=CHCH_2CH=CHCH_2CH=CH(CH_2)_2COOH$], stearic acid [$CH_3CH_2(CH_2)_{15}COOH$], ricinoleic acid [$CH_3(CH_2)_5C(OH)HCH_2CH=CH(CH_2)_7COOH$] etc.

In another embodiment of the present invention, the treated HPPE yarn of the invention also comprises a lipid, wherein the lipid is a fatty acid selected from the group consisting of fatty acids with 6 to 30 carbon atoms in their chemical structure or mixtures thereof, preferably alpha-linolenic acid or arachidonic acid or mixtures thereof.

In another embodiment of the present invention, the treated HPPE yarn of the invention also comprises an oxidizing alkyd.

Alkyd resins (or alkyds) are polyesters prepared from polyols, polyacids and fatty acids. There are many types of alkyds. One classification is into oxidizing and non-oxidizing types. Oxidizing alkyds (or oxidizing alkyd resins) are those alkyds which are crosslinked by the same mechanism as drying oils mentioned herein. In principle, the same type of driers used for drying oils can be also employed to dry oxidizing alkyds. Oxidizing alkyds are herein considered as synthetic drying oils. They are polyesters of one or more polyols such as glycerol, pentaerythritol, one or more polyacids, preferably dibasic acids such as for example terephthalic acid, isophthalic acid, phthalic anhydride and fatty acids from one or more drying or semidrying oils such as for example soybean oil. Oxidizing alkyds can be modified by reaction with vinyl monomers such as for example styrene, vinyl toluene, methyl methacrylate, methyl acrylate, etc.

In one embodiment of the present invention, the treated HPPE yarn also comprises an alkyd.

In a preferred embodiment of the present invention, the treated HPPE yarn also comprises an oxidizing alkyd.

In another embodiment of the present invention, the treated HPPE yarn of the present invention comprises an antimicrobial agent.

In another embodiment of the present invention, the treated HPPE yarn of the present invention comprises an antimicrobial agent and a lipid.

In another embodiment of the present invention, the treated HPPE yarn of the present invention comprises an antimicrobial agent and an alkyd.

In another embodiment of the present invention, the treated HPPE yarn of the present invention comprises an antimicrobial agent and an oxidizing alkyd.

In another embodiment of the present invention, the treated HPPE yarn of the present invention also comprises a lipid and/or an alkyd.

In a preferred embodiment of the present invention, the treated HPPE yarn of the invention also comprises a lipid and/or an oxidizing alkyd.

In another embodiment, the present invention provides for a treated HPPE yarn comprising:
  a porous polyolefin layer that adheres to a surface of a HPPE yarn and covers at least partly the surface of the HPPE yarn;
  a composition comprising an active agent and a lipid and which composition is at least partially absorbed within the porous polyolefin layer.

These treated HPPE yarns have comparable mechanical properties to those of untreated HPPE yarns and moreover present an enhanced adhesion and they are able to deliver active agents such as bioactive agents, thus presenting antimicrobial activity, without also compromising the flexibility of the HPPE yarn.

In yet another embodiment, the present invention provides for a treated HPPE yarn comprising:
  a porous polyolefin layer that adheres to a surface of a HPPE yarn and covers at least partly the surface of the HPPE yarn;
  a composition comprising an active agent and an oxidizing alkyd and which composition is at least partially absorbed within the porous polyolefin layer.

These treated HPPE yarns have comparable mechanical properties to those of untreated HPPE yarns and moreover present an enhanced adhesion and they are able to deliver in an enhanced controlled way (controlled release) active agents such as bioactive agents, thus presenting enhanced controlled antimicrobial activity. In another embodiment, the present invention provides for a treated HPPE yarn comprising:
  a porous polyolefin layer that adheres to a surface of a HPPE yarn and covers at least partly the surface of the HPPE yarn;
  a composition comprising an active agent and a fatty acid and which composition is at least partially absorbed within the porous polyolefin layer.

These treated HPPE yarns have comparable mechanical properties to those of untreated HPPE yarns and moreover present an enhanced adhesion and they are able to deliver active agents such as bioactive agents, thus presenting antimicrobial activity, without also compromising the flexibility of the HPPE yarn.

In yet another embodiment, the present invention provides for a treated HPPE yarn comprising:
  a porous polyolefin layer that adheres to a surface of a HPPE yarn and covers at least partly the surface of the HPPE yarn;
  a composition comprising an active agent and an oil and which composition is at least partially absorbed within the porous polyolefin layer.

These treated HPPE yarns have comparable mechanical properties to those of untreated HPPE yarns and moreover present an enhanced adhesion and they are able to deliver in an enhanced controlled way (controlled release) active agents such as bioactive agents, thus presenting enhanced controlled antimicrobial activity and without also compromising the flexibility of the HPPE yarn.

In a preferred embodiment, the present invention provides for a treated HPPE yarn comprising:
  a porous polyolefin layer that adheres to a surface of a HPPE yarn and covers at least partly the surface of the HPPE yarn;
  a composition comprising a growth factor and a fatty acid and which composition is at least partially absorbed within the porous polyolefin layer.

These treated HPPE yarns have comparable mechanical properties to those of untreated HPPE yarns and moreover present an enhanced adhesion and they are able to deliver a growth factor without also compromising the flexibility of the HPPE yarn.

In a preferred embodiment, the present invention provides for a treated HPPE yarn comprising:
  a porous polyolefin layer that adheres to a surface of a HPPE yarn and covers at least partly the surface of the HPPE yarn;
  a composition comprising a bone inductive agent and which composition is at least partially absorbed within the porous polyolefin layer.

These treated HPPE yarns have comparable mechanical properties to those of HPPE yarns and moreover present an enhanced adhesion and they are able to deliver a bone inductive agent, thus enhancing biocompatibility and bioactivity of a HPPE yarn, without also compromising the flexibility of the HPPE yarn.

In yet another embodiment, the present invention provides for a treated HPPE yarn comprising:
  a porous polyolefin layer that adheres to a surface of a HPPE yarn and covers at least partly the surface of the HPPE yarn;
  a composition comprising an antimicrobial agent, a growth factor, a bone inductive agent and a lipid and which composition is at least partially absorbed within the porous polyolefin layer.

These treated HPPE yarns have comparable mechanical properties to those of HPPE yarns and moreover present an enhanced adhesion and they are able to deliver the growth factor and the antimicrobial agent, thus presenting enhanced controlled antimicrobial activity. In addition, they are able to deliver a bone inductive agent, thus enhancing biocompatibility and bioactivity of a HPPE yarn.

In yet another embodiment, the present invention provides for a treated HPPE yarn comprising:
- a porous polyolefin layer that adheres to a surface of a HPPE yarn and covers at least partly the surface of the HPPE yarn;
- a composition comprising an antimicrobial agent, a growth factor, a bone inductive agent and an oxidizing alkyd and which composition is at least partially absorbed within the porous polyolefin layer.

These treated HPPE yarns have comparable mechanical properties to those of HPPE yarns and moreover present an enhanced adhesion and they are able to deliver in an enhanced controlled way (controlled release), the growth factor and the antimicrobial agent, thus presenting enhanced controlled antimicrobial activity. In addition, they are able to deliver a bone inductive agent, thus enhancing biocompatibility and bioactivity of a HPPE yarn.

In yet another embodiment, the present invention provides for a treated HPPE yarn comprising:
- a porous polyolefin layer that adheres to a surface of a HPPE yarn and covers at least partly the surface of the HPPE yarn;
- a composition comprising an antimicrobial agent, a growth factor, a bone inductive agent and a fatty acid and which composition is at least partially absorbed within the porous polyolefin layer.

These treated HPPE yarns have comparable mechanical properties to those of HPPE yarns and moreover present an enhanced adhesion and they are able to deliver the growth factor and the antimicrobial agent, thus presenting enhanced controlled antimicrobial activity. In addition, they are able to deliver a bone inductive agent, thus enhancing biocompatibility and bioactivity of a HPPE yarn.

In another aspect, the present invention provides for an article comprising a treated HPPE yarn or yarn structure or yarn configuration such as a braid, a textile, a woven, a non-woven, a knitted, a braided or otherwise formed structure comprising the treated HPPE yarn or consisting of the treated HPPE yarn, of the present invention.

In another aspect, the present invention provides for an article comprising a treated HPPE yarn, preferably a suture, a medical cable or a medical mesh such as a hernia mesh.

In another aspect, the invention provides for a device comprising a treated HPPE yarn of the present invention.

In yet another embodiment, the present invention provides for a device comprising an article as defined above, preferably a medical device comprising a suture and at least one of a needle and an anchor.

Preferably, surgical sutures should have a high purity since it is used for stitching wound, which is susceptible to infection. A suture consisting of the yarn according to the present invention is especially advantageous because of its purity and less risk of attracting bacteria. Monofilaments have a stiff and smooth surface, which combine to reduce entanglement. This is also an advantage during the operation of closing wounds.

In another aspect, the present invention provides for the use of:
- a treated HPPE yarn of the present invention;
- an article of the present invention; or
- a device of the present invention, for automotive applications (car parts, composite structures, ceramic structures, etc.), marine applications (ships, boats, rigging in yachting/ships, sails, slings, fishing lines, cables, composite structures, ceramic structures, biomimetics, etc.), aerospace applications (planes, helicopters, composite structures, ceramic structures, etc.), medical applications (joint arthroplasty, orthopedic and spine implants, for example meniscus implants, surgical sutures, meshes for example hernia meshes, fabrics, woven or non-woven sheets, tapes, ribbons, bands, artificial joints, cables such as trauma fixation cables, sternum closure cables, prophylactic or per prosthetic cables, long bone fracture fixation cables, small bone fracture fixation cables, tube-like products for e.g. ligament replacement, endless loop products, bag-like, balloon-like products, composite structures, ceramic structures, etc.), defense applications (ballistic protection, body armor, ballistic vests, ballistic helmets, ballistic vehicle protection, composite structures, ceramic structures, etc.), sports/recreational applications (fencing, skates, skateboarding, snowboarding, suspension lines on sport parachutes, paragliders, kites, kite lines for kite sports, climbing equipment, bow strings, racquet strings, spear lines for spear guns, edge protection on rinks and boards, composite structures, ceramic structures, etc.), architectural applications (windows, doors, (pseudo-)walls, cables, etc.), clothing (gloves, protective clothing/equipment, textiles, textile composite structures, textile ceramic structures etc.), bottling applications, machinery applications (can and bottle handling machine parts, moving parts on weaving machines, bearings, gears, composite structures, ceramic structures, etc.).

In yet another embodiment, the invention provides for the use of the treated HPPE yarn of the present invention for automotive applications (car parts, composite structures, ceramic structures, etc.), marine applications (ships, boats, rigging in yachting/ships, sails, slings, fishing lines, cables, composite structures, ceramic structures, etc.), aerospace applications (planes, helicopters, composite structures, ceramic structures, etc.), medical applications (joint arthroplasty, orthopedic and spine implants, for example meniscus implants, surgical sutures, meshes for example hernia meshes, fabrics, woven or non-woven sheets, tapes, ribbons, bands, artificial joints, cables such as trauma fixation cables, sternum closure cables, prophylactic or per prosthetic cables, long bone fracture fixation cables, small bone fracture fixation cables, tube-like products for e.g. ligament replacement, endless loop products, bag-like, balloon-like products, composite structures, ceramic structures, biomimetics, etc.), defense applications (ballistic protection, body armor, ballistic vests, ballistic helmets, ballistic vehicle protection, composite structures, ceramic structures, etc.), sports/recreational applications (fencing, skates, skateboarding, snowboarding, suspension lines on sport parachutes, paragliders, kites, kite lines for kite sports, climbing equipment, bow strings, racquet strings, spear lines for spear guns, edge protection on rinks and boards, composite structures, ceramic structures, etc.), architectural applications (windows, doors, (pseudo-)walls, cables, etc.), clothing (gloves, protective clothing/equipment, textiles, textile composite structures, textile ceramic structures etc.), bottling applications, machinery applications (can and bottle handling machine parts, moving parts on weaving machines, bearings, gears, composite structures, ceramic structures, etc.), wherein the treated HPPE yarn is used in an amount and in a format that allows the treated HPPE yarn to exhibit its mechanical, antimicrobial and/or adhesion properties.

Another aspect of the invention is treated HPPE yarns and yarn structures such as braids according to the Examples 4 to 7 and Examples 9 to 12, described herein.

Yet, another aspect of the invention is an article according to the Examples 4 to 7 and Examples 9 to 12.

An individual feature or combination of features from an embodiment of the invention described herein, as well as obvious variations thereof, are combinable with or exchangeable for features of the other embodiments described herein, unless the person skilled in the art would immediately realise that the resulting embodiment is not physically feasible.

Further aspects of the invention and preferred features thereof are given in the claims herein.

The present invention will now be described in detail with reference to the following non limiting examples which are by way of illustration only.

EXAMPLES

In Examples 1, 3 and 8 the compositions did not comprise any active agent. In Example 2, the composition comprised only triclosan as active agent. In Examples 4 to 7 and 9 to 12, the composition comprised triclosan as active agent and either alpha-linolenic acid or arachidonic acid as lipids. The alpha-linolenic acid and arachidonic acids are fatty acids.

The simultaneous RF plasma polymerisation and gas etching of the Dyneema Purity® braids were carried out at EMPA (Swiss Materials Science & Technology, Lerchenfeldstrasse 5, CH-9014, St. Gallen, Switzerland).

Methods & Techniques for Assessing Properties Related to HPPE Braids Assessment of Mechanical Properties of the HPPE Braids The elongation at break (%), E-modulus (GPa), force-at-maximum break ($F_{max}$) (N) of the tested HPPE braids were measured as follows: a specimen of braid was extended until breakage using a tensile testing machine, and the breaking force and the elongation at break are recorded. The sample preparation and conditioning were done as follows: before testing, the bobbins are conditioned for at least two hours at 21° C.±1° C. and relative humidity between 40 and 75%. The HPPE braids were taken from the bobbin and placed directly into the clamps of the tensile testing machine. Any change in twist of the specimen is avoided as well as touching the part to be tested with bare hands. The actual tensile testing was carried out as follows: the tensile testing machine, Zwick 1435, was operated with a constant extension rate. The machine was equipped with Instron clamps 5681C and stainless steel clamping blocks. The clamping pressure was 6.8 bar. The extension rate was 250 mm/min and the gage length is 500 mm. A load cell with a maximum force of 1 kN was used. A pretension of 0.2 cN/dtex was applied to remove any slack from the braid.

The maximum force-at-break ($F_{max}$) (cN, centiNewton) was the maximum force applied to rapture the sample. The elongation at break (%) was determined by 100 times the displacement of the clamps (ΔL) expressed in mm divided by the gage length ($L_o$) (500 mm). The elongation at break was not corrected for the pretension. The E-modulus (GPa) was determined by the specific stress difference (ΔF, measured in cN/dtex) between 0.3 and 1% elongation divided by the difference in elongation (0.7%) multiplied by $10^{-1}$ and subsequently multiplied the linear density of the material (measured in g/cm³) the yarn is made of. Average values for the elongation at break, E-modulus, force-at-maximum break were calculated using data from five individual tensile tests. The specific stress is determined according to the Handbook of Fibre Rope Technology, as follows:

specific stress=tension/(linear density), measured in MN/(kg/m) equal to N/tex.

Assessment of Adhesion of the Composition onto the HPPE Braids

The adhesion of the composition onto the HPPE braids was checked by means of antimicrobial activity testing. After incubation of the braid comprising the composition which composition comprised a fatty acid and triclosan, the loss of the fatty acid and triclosan in the agar is reflected in a loss of antimicrobial activity of the braid. The Ref-HPPE braid and C:H:N or C:H:O treated HPPE braids comprising a fatty acid (alpha-linolenic acid and triclosan or arachidonic acid and triclosan) were incubated in non-inoculated agar at 37° C. for 8 days, and subsequently the braid was transferred to inoculated agar to assess its antimicrobial activity according the method described below (see Assessment of antimicrobial activity of the HPPE braids).

Assessment of Antimicrobial Activity of the HPPE Braids

*Escherichia coli* ATCC 11105 was cultured from frozen stock in sterile Luria Bettani medium. The bacterial suspension had a concentration of about $10^9$ CFU/mL. LB agar plates were inoculated with 100 µL of this bacterial suspension. The HPPE braids were cut into approximate 5 cm lengths; straight sections of HPPE braids were used. Each braid was pressed in the agar with sterile forceps to optimise contact with the agar surface. The agar plates were subsequently incubated at 37° C. for 24 h in an exicator filled with a saturated salt solution to prevent dehydration of the agar. The width of the zone of growth inhibition at right angles to the braid length was recorded to nearest 1 mm at three spots along the suture and photographic images of the agar plates were generated.

Assessment of Anti-Microbial Activity of the HPPE Braids for 3.5 Months: Simulation of In-Vivo Anti-Microbial Activity:

*Escherichia coli* ATCC 11105 was cultured from frozen stock in sterile Luria Bettani medium. The bacterial suspension had a concentration of about $10^9$ CFU/mL. LB agar plates were inoculated with 100 µL of this bacterial suspension. The HPPE braids were cut into approximate 5 cm lengths; straight sections of HPPE braids were used. Each braid was pressed in the agar with sterile forceps to optimise contact with the agar surface. The agar plates were subsequently incubated at 37° C. for 24 h in an exicator filled with a saturated salt solution to prevent dehydration of the agar. Upon assessing the zone of inhibition of each sample and without changing the position of the braids in the agar plates, the braids in test were kept in the inoculated agar at 37° C. for additional 105 days. Longer testing was not possible due to the reduced quality of the agar with time. The zone of inhibition was assessed again. The width of the zone of growth inhibition at right angles to the suture length was recorded to nearest 1 mm at three spots along the braid and photographic images of the agar plates were generated.

Examples 1-12

Example 1

Reference HPPE Braid (Ref-HPPE)

Dyneema Purity® SGX 110 dtex TS100 is an untreated HPPE yarn. Dyneema Purity® SGX 110 dtex TS100 yarn was used to form 8×1×110 braids, called herein after "Dyneema Purity® braids".

Untreated Dyneema Purity® braid was used as a reference HPPE braid.

Table 1 presents the properties of Dyneema Purity® SGX 110 dtex TS100 yarn along with the test methods used to measure these properties.

TABLE 1

| Property | Value | Test Method |
|---|---|---|
| Density | 0.97 g/mL | ASTM D792-00 |
| Melting Temperature | 147° C. | ASTM F2625-07 |
| Coeficient of friction, dry | 0.09 | ASTM D3412-07 |
| Linear density | 110 dtex | ASTM D1907-07 |
| No. of filaments | 50 | n.a. |
| Single filament density | 2.2 dtex | n.a. |
| Diameter of single filament | 17 microns | Optical Microscopy |
| Load at break | 36 N | ISO 2062-93 and ASTM D2256-02 |
| Tenacity at break | 33 cN/dtex | ISO 2062-93 and ASTM D2256-02 |
| E-modulus | 97 GPa or 1000 cN/dtex | ISO 2062-93 and ASTM D2256-02 |
| Elongation at break | 3.5% | ISO 2062-93 and ASTM D2256-02 |
| Twist level & direction | 100 S turns/meter | ASTM D1423-02 |

Example 2

Dyneema Purity® Braid Comprising Alpha-Linolenic Acid: Ref-HPPE-L-TRI-2.9

Dyneema Purity® braids (8×1×110) was dip-coated (10 min at 23° C.) in a 6.0 g/L alpha-linolenic acid solution in ethyl acetate containing 2.9 g/L (grams per liter) triclosan (see Table 2). The resulting braid was dried at 23° C.

Example 3

C:H:N treated Dyneema Purity® Braid: CHN-HPPE

Dyneema Purity® braids (8×1×110) were treated by simultaneous RF plasma polymerisation and gas etching. A porous polyolefin film of 60 nm thickness was deposited to a upon exposure at a volume ratio of $NH_3/C_2H_4$ 1:1 v/v, pressure of 10 Pa, power input of 0.06 W/cm$^2$ and exposure time 24 min.

Examples 4-6

C:H:N Treated Dyneema Purity® Braids with the Composition Comprising Alpha-Linolenic Acid and Triclosan: CHN-HPPE-L-TRI-1.0, CHN-HPPE-L-TRI-2.0 and CHN-HPPE-L-TRI-2.9

Dyneema Purity® braids (8×1×110) of Example 3 were further dip-coated for 10 min at 23° C. in a 6.0 g/L alpha-linolenic acid solution in ethyl acetate containing a certain amount of triclosan (see Table 2). The resulting braids were dried at 23° C.

Example 7

C:H:N Treated Dyneema Purity® Braids with Arachidonic Acid and Triclosan: CHN-HPPE-A-TRI-2.0

Dyneema Purity® braids (8×1×110) were further dip-coated for 10 min at 23° C. in a 6.0 g/L arachidonic acid solution in ethyl acetate containing 2.0 g/L triclosan (see Table 2). The resulting braids were dried at 23° C.

Example 8

C:H:O Treated Dyneema Purity® Braid: CHO-HPPE

Dyneema Purity® braids (8×1×110) were treated by simultaneous RF plasma polymerisation and gas etching. A porous polyolefin film of 60 nm thickness was deposited to a upon exposure at a volume ratio of $CO_2/C_2H_4$ 4:1 v/v, pressure of 10 Pa, power input of 0.07 W/cm$^2$ and exposure time 30 min.

Examples 9-11

C:H:O Treated Dyneema Purity® Braids with the Composition Comprising Alpha-Linolenic Acid and Triclosan: CHO-HPPE-L-TRI-1.0, CHO-HPPE-L-TRI-2.0 and CHO-HPPE-L-TRI-2.9

Dyneema Purity® braids (8×1×110) of Example 8 were further initially treated by simultaneous vacuum plasma polymerisation and plasma etching (C:H:O treatment). Subsequently, the braids were dip-coated for 10 min at 23° C. in a 6.0 g/L alpha-linolenic acid solution in ethyl acetate containing a certain amount of triclosan (see Table 2). The resulting braids were dried at 23° C.

Example 12

C:H:O Treated Dyneema Purity® Braids with Arachidonic Acid and Triclosan: CHO-HPPE-A-TRI-2.0

Dyneema Purity® braids (8×1×110) of Example 8 were further dip-coated for 10 min at 23° C. in a 6.0 g/L arachidonic acid solution in ethyl acetate containing 2.0 g/L triclosan (see Table 2). The resulting braids were dried at 23° C.

TABLE 2

| | | | COMPOSITION | | ANTIMICROBIAL PROPERTIES | | | MECHANICAL PROPERTIES | | |
|---|---|---|---|---|---|---|---|---|---|---|
| | | | | | Prior incubation time in non-inoculated agar | | in vivo simulation (incubation time in agar) | | | |
| | | | | | 0 days Size of | 8 days Size of | 105 days Size of | | | |
| | | | | Active Agent (Triclosan) (g/L) | Growth inhibition zone (mm) | Growth inhibition zone (mm) | Growth inhibition zone (mm) | $F_{max}$ (N) | Elongation at break (%) | E-modulus (GPa) |
| Ex. | Braid | C:H:N or C:H:O Treated | Lipid (Fatty acid) | | | | | | | |
| 1 | Ref-HPPE | No | None | 0.0 | 0 | 0 | 0 | 248 | 3.7 | 72.0 |
| 2 | Ref-HPPE-L-TRI-2.9 | No | alpha-Linolenic acid | 2.9 | 15 | 0 | 15 | 246 | 3.5 | 72.1 |
| 3 | CHN-HPPE | Yes | None | 0.0 | 0 | 0 | 0 | 243 | 3.4 | 72.6 |

TABLE 2-continued

| | | | COMPOSITION | | ANTIMICROBIAL PROPERTIES | | | MECHANICAL PROPERTIES | | |
|---|---|---|---|---|---|---|---|---|---|---|
| | | | | Active Agent (Triclosan) (g/L) | Prior incubation time in non-inoculated agar | | in vivo simulation (incubation time in agar) | | | |
| | | | | | 0 days Size of Growth inhibition zone (mm) | 8 days Size of Growth inhibition zone (mm) | 105 days Size of Growth inhibition zone (mm) | | | |
| Ex. | Braid | C:H:N or C:H:O Treated | Lipid (Fatty acid) | | | | | $F_{max}$ (N) | Elongation at break (%) | E-modulus (GPa) |
| 4 | CHN-HPPE-L-TRI-1.0 | Yes | alpha-Linolenic acid | 1.0 | 10 | 2 | 10 | 245 | 3.5 | 72.8 |
| 5 | CHN-HPPE-L-TRI-2.0 | Yes | alpha-Linolenic acid | 2.0 | 13 | 3 | 13 | 244 | 3.4 | 72.9 |
| 6 | CHN-HPPE-L-TRI-2.9 | Yes | alpha-Linolenic acid | 2.9 | 15 | 4 | 15 | 246 | 3.4 | 72.6 |
| 7 | CHN-HPPE-A-TRI-2.0 | Yes | Arachidonic acid | 2.0 | 13 | 3 | 13 | 242 | 3.5 | 72.7 |
| 8 | CHO-HPPE | Yes | None | 0.0 | 0 | 0 | 0 | 238 | 3.4 | 72.9 |
| 9 | CHO-HPPE-L-TRI-1.0 | Yes | alpha-Linolenic acid | 1.0 | 10 | 2 | 10 | 238 | 3.5 | 73.0 |
| 10 | CHO-HPPE-L-TRI-2.0 | Yes | alpha-Linolenic acid | 2.0 | 12 | 3 | 12 | 240 | 3.5 | 72.8 |
| 11 | CHO-HPPE-L-TRI-2.9 | Yes | alpha-Linolenic acid | 2.9 | 16 | 4 | 16 | 238 | 3.4 | 72.9 |
| 12 | CHO-HPPE-A-TRI-2.0 | Yes | Arachidonic acid | 2.0 | 12 | 3 | 12 | 241 | 3.5 | 72.0 |

Upon comparing data presented in Table 2, the following can be concluded:

a. All C:H:N or C:H:O treated HPPE braids comprising an active agent such as triclosan presented comparable mechanical properties in comparison to those of the Ref-HPPE braid.

For example, upon comparing the mechanical properties of the HPPE braid of Example 1 (Ref-HPPE) with the mechanical properties of any of the HPPE braids of Examples 4 to 7 or Examples 9 to 12, it is clear that the C:H:N or C:H:O treated HPPE braids comprising alpha-linolenic acid and triclosan presented comparable mechanical properties to those of the reference braid (Ref-HPPE).

b. Only the HPPE braids with the composition comprising an active agent such as triclosan presented antimicrobial activity.

The growth of the tested E. coli strain is not inhibited by the Ref-HPPE braid nor by the CHN- or CHO-HPPE braids. Only braids comprising triclosan presented antimicrobial activity (compare Antimicrobial Properties/Prior Incubation Time equal to 0 days of Examples 1, 3 and 8 with Antimicrobial Properties/Prior Incubation Time equal to 0 days of Examples 2, 4 to 7 and 9 to 12). Larger inhibition zones were found for braids with higher triclosan content.

c. Only the C:H:N or C:H:O treated HPPE braids comprising also an active agent such as triclosan presented enhanced adhesion of the composition in respect to the HPPE braids which had either no C:H:N or C:H:O treatment or no active agent (compare Antimicrobial Properties/Prior Incubation Time equal to 8 days of Examples 1, 2, 3 and 8 with Antimicrobial Properties/Prior Incubation Time equal to 8 days of Examples 4 to 7 and 9 to 12).

All C:H:N or C:H:O treated HPPE braids with the composition comprising alpha-linolenic acid and triclosan or arachidonic acid and triclosan remained antimicrobial active against the tested E. coli strain after 8 days of pre-incubation at 23° C. in agar, followed by transfer to fresh agar. For example, upon comparing the antimicrobial activity of Ref-HPPE-L-TRI-2.9 with either CHN-HPPE-L-TRI-2.9 or CHO-HPPE-L-TRI-2.9, it becomes evident that the C:H:N or C:H:O treated braids comprising alpha-linolenic acid and triclosan presented enhanced adhesion over the untreated Ref-HPPE-L-TRI-2.9.

From the above a., b. and c. conclusions, it becomes clear that only the C:H:N or C:H:O treated HPPE braids with the composition comprising a lipid (in this series of Examples fatty acids such as alpha-linolenic acid or arachidonic acid consisted the lipid of the composition) and an active agent (in this series of Examples triclosan was the active agent) presented a combination of good mechanical properties—that are comparable to the mechanical properties of an untreated HPPE braid—and at the same time antimicrobial activity and enhanced adhesion of the composition comprising a lipid and an active agent.

The invention claimed is:

1. A treated high performance polyethylene (HPPE) yarn comprising:
   a HPPE yarn,
   a porous polyolefin layer having a thickness of at least 5 nm and at most 1000 nm that adheres to and at least partly covers a surface of the HPPE yarn; and
   a composition comprising an active agent, wherein the composition is at least partially absorbed within the porous polyolefin layer.

2. The treated HPPE yarn according to claim 1, wherein the treated HPPE yarn also comprises a lipid and/or an alkyd.

3. The treated HPPE yarn according to claim 2, wherein the lipid is a fatty acid selected from the group consisting of fatty acids with 6 to 30 carbon atoms in their chemical structure or mixtures thereof.

4. The treated HPPE yarn according to claim 3, wherein the lipid is a fatty acid selected from the group consisting of alpha-linolenic acid, arachidonic acid and mixtures thereof.

5. The treated HPPE yarn according to claim 1, wherein the active agent is an antimicrobial agent.

6. The treated HPPE yarn according to claim 5, wherein the active agent is triclosan.

7. The treated HPPE yarn according to claim 1, wherein the treated HPPE yarn further comprises a growth factor.

8. The treated HPPE yarn according to claim 1, wherein the treated HPPE yarn has a diameter which is less than 50 μm.

9. The treated HPPE yarn according to claim 8, wherein the diameter of the treated HPPE yarn is less than 30 μm.

10. An article comprising the treated HPPE yarn as defined in claim 1.

11. The article according to claim 10, wherein the article is a suture, a medical cable or a medical mesh.

12. The article according to claim 11, wherein the medical mesh is a hernia mesh.

13. A medical device comprising an article as defined in claim 10, wherein the medical device further comprises a suture and at least one of a needle and an anchor.

14. A method for making a treated high performance polyethylene (HPPE) yarn, comprising the steps of:
   (a) providing a HPPE yarn comprised of HPPE filaments;
   (b) forming a pre-treated HPPE yarn by depositing via simultaneous plasma polymerisation and plasma etching, a porous polyolefin layer having a thickness of at least 5 nm and at most 1000 nm that adheres to and at least partly covers a surface of the HPPE yarn; and thereafter
   (b) forming a treated HPPE yarn by depositing a composition comprising an active agent to the pre-treated HPPE yarn at an effective temperature and for an effective time sufficient to prevent loss of molecular orientation of the HPPE filaments of the HPPE yarn by filament softening or a start of filament melting.

15. The method according to claim 14, comprising the further step of:
   (d) using the treated HPPE yarn to prepare a yarn structure or yarn configuration such as a braid, a textile, a woven, a non-woven, a knitted, a braided or otherwise formed structure comprising the treated HPPE yarn or consisting of the treated HPPE yarn.

16. The method according to claim 14, wherein the simultaneous plasma polymerisation and plasma etching is carried out in the presence of the HPPE yarn, an alkene gas, an inert gas, and either carbon dioxide ($CO_2$) or ammonia (NH3).

17. The method according to claim 16, wherein the alkene gas is ethylene or a mixture of alkene gases.

18. The method according to claim 16, wherein the inert gas is argon or a mixture of inert gases.

19. The method according to claim 14, wherein step (a) is practiced by depositing the composition comprising an active agent at a temperature of at least 10° C. and at most 90° C. during a time of at least 10 seconds and at most 60 minutes.

20. The method according to claim 14, which comprises converting the HPPE yarn into a yarn structure or yarn configuration prior to the step (b) of depositing the composition comprising the active agent.

* * * * *